United States Patent
Flaherty

(10) Patent No.: US 6,589,164 B1
(45) Date of Patent: Jul. 8, 2003

(54) STERILITY BARRIERS FOR INSERTION OF NON-STERILE APPARATUS INTO CATHETERS OR OTHER MEDICAL DEVICES

(75) Inventor: J. Christopher Flaherty, Los Altos, CA (US)

(73) Assignee: TransVascular, Inc., Menlo Park, CA (US)

( * ) Notice: Subject to any disclaimer, the term of this patent is extended or adjusted under 35 U.S.C. 154(b) by 0 days.

(21) Appl. No.: 09/505,149

(22) Filed: Feb. 15, 2000

(51) Int. Cl.[7] ................................................. A61B 1/04
(52) U.S. Cl. .......................... 600/121; 604/21; 604/171
(58) Field of Search ................................. 604/171, 187, 604/198–199, 197, 263, 20–22; 600/164.01, 437, 439, 459, 461–467, 101, 103, 104, 106, 108, 117, 118, 121, 123, 129, 136, 137, 139, 160

(56) References Cited

U.S. PATENT DOCUMENTS

| | | | |
|---|---|---|---|
| 3,825,001 A | * 7/1974 | Bennet et al. ............... 604/163 |
| 4,326,520 A | * 4/1982 | Alley .......................... 604/159 |
| 4,327,723 A | * 5/1982 | Frankhouser ................ 604/171 |
| 4,593,699 A | * 6/1986 | Poncy et al. ................. 206/305 |
| 4,834,710 A | * 5/1989 | Fleck ........................... 604/163 |
| 4,877,033 A | * 10/1989 | Seitz, Jr. ...................... 128/846 |
| 5,168,863 A | * 12/1992 | Kurtzer ........................ 206/363 |
| 5,235,987 A | * 8/1993 | Wolfe .......................... 600/461 |
| 5,474,075 A | * 12/1995 | Goldberg et al. ............ 600/463 |
| 5,507,295 A | * 4/1996 | Skidmore .................... 600/121 |
| 5,873,828 A | * 2/1999 | Fujio et al. .................. 600/439 |
| 6,193,666 B1 | * 2/2001 | Ouchi .......................... 600/459 |
| 6,238,336 B1 | * 5/2001 | Ouchi .......................... 600/104 |

FOREIGN PATENT DOCUMENTS

WO WO99/48424 * 9/1999

* cited by examiner

Primary Examiner—Michael J. Hayes
Assistant Examiner—LoAn H. Thanh
(74) Attorney, Agent, or Firm—Robert D. Buyan; Stout, Uxa, Buyan & Mullins, LLP

(57) ABSTRACT

Methods, apparatus and systems wherein the distal portion of an elongate apparatus (e.g., a catheter or cannula) having a sealed lumen (e.g., a blind lumen) formed therein is insertable into the body of a mammalian patient and a tubular sterility barrier is attached to or formed on the proximal portion of the elongate apparatus. The tubular sterility barrier is arranged so that it extends outside of a sterile field that is being maintained around the proximal portion of the elongate device. A non-sterile working apparatus (e.g., an intravascular ultrasound device or other imaging apparatus, etc.) may then be inserted through the sterility barrier and into the sealed lumen without causing contamination of the sterile field or the patient.

21 Claims, 10 Drawing Sheets

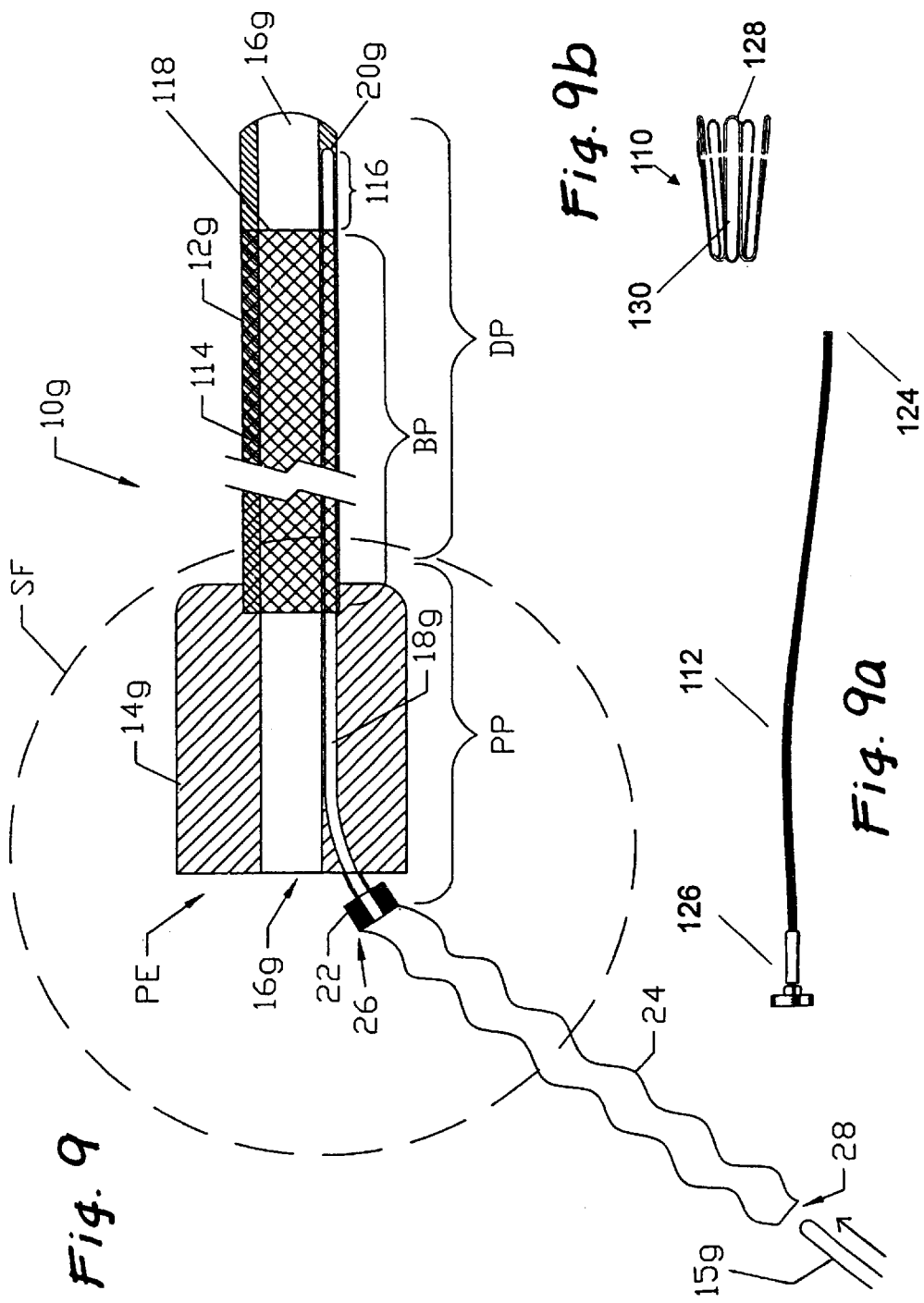

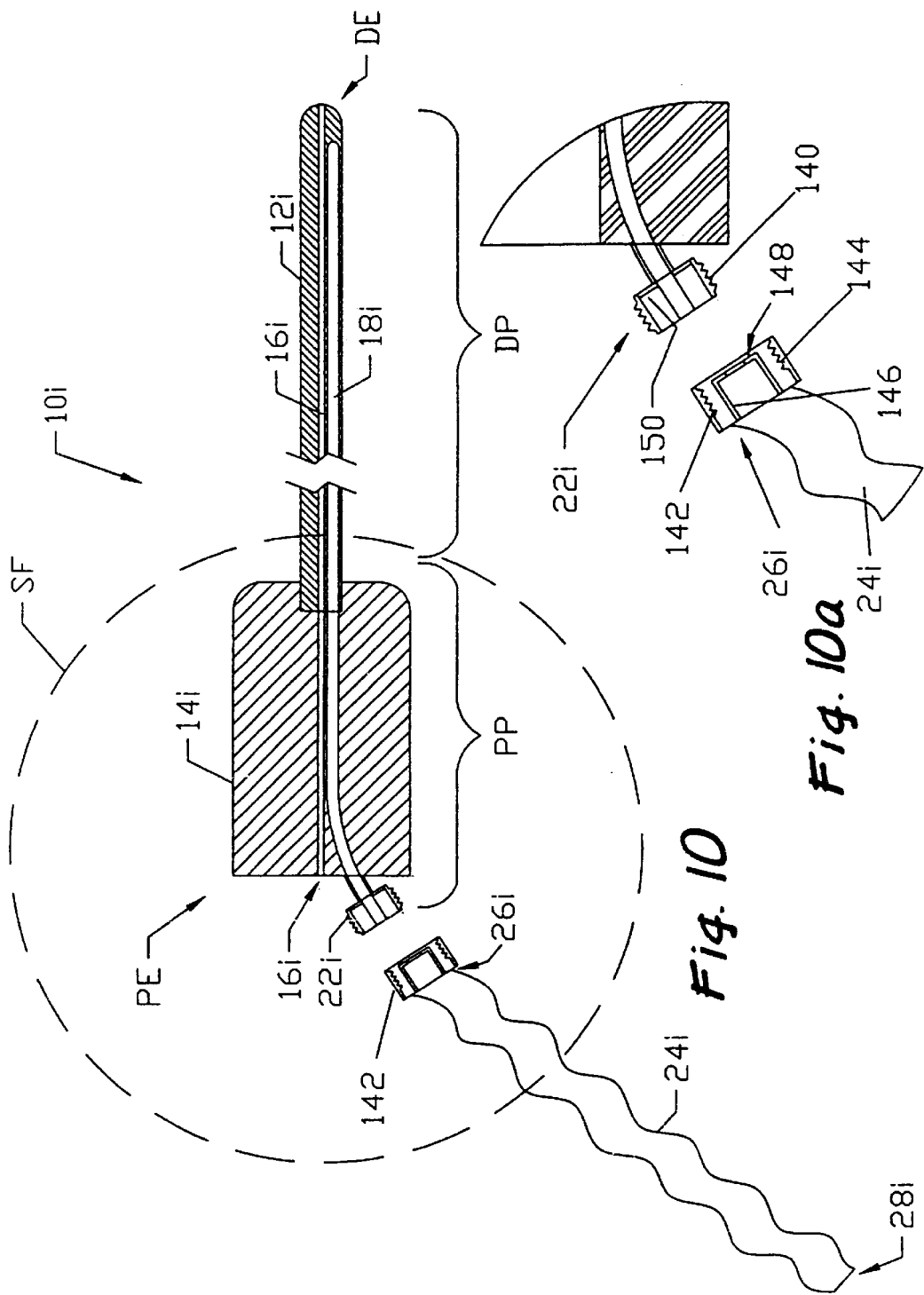

STERILITY BARRIERS FOR INSERTION OF NON-STERILE APPARATUS INTO CATHETERS OR OTHER MEDICAL DEVICES

FIELD OF THE INVENTION

The present invention relates generally to medical devices and methods, and more particularly to the construction and use of a sterility barrier that allows non-sterile apparatus to be inserted into a lumen of a previously inserted catheter (e.g, a flexible catheter or rigid cannula) without contaminating the patient and while maintaining a sterile field around the exteriorized proximal end of the catheter.

BACKGROUND OF THE INVENTION

In modern medical practice, and particularly in the fields of interventional cardiology and interventional radiology, it is sometimes desirable to insert non-sterile apparatus (e.g., an imaging apparatus, scope, sensor, emitter, rotating drive member, etc.) into a sealed lumen of a sterile catheter or cannula that may have already been placed in a blood vessel or other anatomical conduit of a patient's body. Such insertion of the non-sterile apparatus may be problematic due to the need to maintain a sterile operative field around the exteriorized proximal portion of the catheter and to prevent introduction of microbes into the blood or body of the patient.

Examples of some types of procedures in which it may be desirable to insert non-sterile apparatus (e.g., an imaging apparatus, scope, sensor, heater, cooler, sensor, drive member, etc.) into a sealed lumen of a sterile catheter that has been placed in a blood vessel or other anatomical conduit of a patient's body include, but are not necessarily limited to, intravascular ultrasound imaging (IVUS) procedures, balloon angioplasty procedures, stent implantation procedures, atherectomy procedures, embolectomy procedures, and various interventional procedures wherein puncture tracts or channels (e.g., bloodflow passageway(s)) are formed between blood vessels, or between a blood vessel and another target location, using transluminally advanceable tissue penetrating catheters as described in U.S. Pat. Nos. 5,830,222 and 6,283,951. These relatively new procedures include percutaneous, transluminal techniques for bypassing obstructions in coronary or peripheral arteries through the use of the adjacent vein(s) as in situ bypass conduit(s), and other means of revascularizing oxygen starved tissues or delivering therapeutic substances to vessels, tissue and other organs. As explained in U.S. Pat. Nos. 5,830,222 and 6,283,951, some of these procedures may be performed by a vein-to-artery approach wherein a tissue penetrating catheter is inserted into a vein and the desired arterio-venous passageway is initially formed by passing a tissue penetrating element (e.g., a flow of energy or an elongate penetration member) from a catheter, through the wall of the vein in which the catheter is positioned, and into the lumen of an adjacent artery. Alternatively, some of these procedures may be performed by an artery-to-vein approach wherein the catheter is inserted into an artery and the desired arterio-venous passageway is initially formed by passing a tissue penetrating element (e.g., a flow of energy or elongate penetration member) from the catheter, through the wall of the artery in which the catheter is positioned, and into the lumen of an adjacent vein. In addition, it may be advantageous to direct a penetrating element directly into other anatomical structures such as the myocardium, pericardium, chamber of the heart or other organs to deliver a therapeutic agent to the target location, to implant an electrode, sensor or other device at the target location, or for other reasons as described in U.S. Pat. No. 6,283,951.

One factor that may give rise to the desirability of inserting a non-sterile apparatus into a previously-inserted sterile catheter is expense. Indeed, many types of interventional catheters and other medical apparatus are expensive to purchase. When such catheters and other medical apparatus are required to be sterile, they are often times not re-useable, but rather are manufactured as disposable items that may be used only once and then must be discarded. The expense of such single-use, disposable apparatus can result in avoidance of their use by medical practitioners, even in cases where patients may benefit from their use. For example, intravascular ultrasound imaging (IVUS) catheters typically cost between $500.00 to $800.00 each when purchased by a hospital or health-care institution in the United States and are typically supplied as single-use, disposable items. Several published reports have established that the outcomes of coronary stent implantation procedures may be significantly improved by the use of IVUS. see, Goldberg, S. L. et al.; *Benefit of Intracoronary Ultrasound in the Deployment of Palmaz-Schatz Stents,* J. Am. Coll. Cardiol 1994 October; 24(4):996–1003; de Jaegere, P. et al., *Intravascular Ultrasound-Guided Optimized Stent Deployment,* Eur. Heart J. 1998 August; 19(8):1214–23; Schiele, F. et al. *Impact of Intravascular Ultrasound Guadance in Stent Deployment on 6 Month Restenosis Rate,* J. Am. Coll. Cardiol. 1998 August;32(2):320–8 and Balasini, R. et al., *Restenosis Rate After Intravascular Ultrasound-Guided Coronary Stent Implantation,* Cathet. Cardiovasc. Diagn. 1998 August;44 (4):380–6. However, despite this potential benefit to patients, IVUS is not currently used in most coronary stent implantation procedures. The expense associated with the use of IVUS is believed to be the reason why IVUS is not used in more stent implantaion procedures.

Another factor that may give rise to the desirability of inserting a non-sterile apparatus into a previously-inserted sterile catheter is the need for flexibility and/or small diameter of the catheter. For example, in interventional procedures where a catheter must be inserted through highly tortuous blood vessels or into vessels of very small diameter, such as those of the brain, it is desirable for the catheter to be of the smallest diameter and greatest flexibility possible. Because the inclusion of working apparatus (e.g., sensors, drive shafts, wires, ultrasound transducers, etc.) within the body of the catheter can result in increased diameter and/or decreased flexibility of the catheter, it may be desirable to insert such working apparatus after the catheter has been inserted and advanced to its desired location. Sterilization of such working apparatus prior to insertion into the catheter may be difficult or impossible due to the material and/or construction of the working apparatus. Thus, in such cases, it may be desirable to insert the non-sterile working apparatus into the catheter after the catheter has been inserted into and positioned within the patient, without contaminating the patient or the sterile operative field maintained in the area of the site at which the catheter enters the patient's body.

The prior art has included various apparatus and methods for creating sterility barriers to prevent contamination of patients and/or medical devices, including those apparatus and methods described in U.S. Pat. No. 5,385,495 (Lynn), U.S. Pat. No. 5,775,328 (Lowe et al.), U.S. Pat. No. 4,491, 137 (Jingu), U.S. Pat. No. 4,646,772 (Silverstein et al.), U.S. Pat. No. 4,898,178 (Wedel), U.S. Pat. No. 5,341,810

(Dardel), U.S. Pat. No. 5,490,522 (Dardel), U.S. Pat. No. 5,498,230 (Adair) and PCT International Publication Nos. WO84/03034 (Drue et al.), WO97/49337 (Loxe et al.) And WO99/48424 (Lowe et al.). However, none of these apparatus or methods of the prior art are believed to disclose or teach means for inserting a non-sterile elongate apparatus through a sterile field and into a previously inserted sterile catheter, without contaminating either the sterile field or the patient.

Accordingly, there exists a need in the art for the development of apparatus and techniques that will facilitate the insertion of non-sterile apparatus into a lumen of a catheter (e.g, flexible catheter or rigid cannula) without contaminating the patient and while maintaining a sterile field around the proximal end of the catheter.

SUMMARY OF THE INVENTION

A device of the present invention generally comprises a) an elongate apparatus (e.g., a flexible catheter, rigid cannula, probe or other apparatus or member) that has a distal portion that is insertable into the body of a mammalian patient and that has an entry port formed proximal to the distal portion, b) a lumen that extends from the entry port into the distal portion of the elongate apparatus, at least the portion of that lumen that resides within the distal portion of the elongate apparatus being sealed such that any microbes that become introduced thereinto will not escape into the patient's body and c) a generally tubular sterility barrier, one end of which is secured about the entry port such that a non-sterile working apparatus may be passed through the tubular sterility barrier, through the entry port and into the lumen of the elongate apparatus. The sterility barrier is constructed and sealed to the elongate apparatus such that any microbes or other contamination (e.g., lint, dust, particulate matter, residues of chemical agents, parasites, mold spores, other biological matter, etc.) that becomes introduced into the interior of the tubular sterility barrier by such insertion of the non-sterile working apparatus therethrough will remain and be contained therein.

Further in accordance with the invention there is provided a method for using the device of the foregoing character to perform a procedure wherein a sterile field is to be maintained around a site at which the elongate apparatus (e.g., a flexible catheter, rigid cannula, probe or other apparatus or member) of the device enters the body of a mammalian patient. This method generally comprises the steps of a) providing a device of the foregoing character that is sterile, b) providing a working apparatus that is sized to pass into the lumen of the elongate apparatus to perform some desired function from a position within that lumen, c) inserting the elongate apparatus into the patient's body and establishing a sterile field adjacent to that site, d) positioning the sterility barrier such that it extends through the sterile field with its second end located outside of the sterile field, e) advancing the working apparatus into the first end of the sterility barrier, through the sterility barrier, through the entry port and into the lumen of the elongate apparatus, and e) using the working apparatus to perform its desired function. The steps of this method need not necessarily be performed in the order stated in this paragraph, but rather may be performed in any suitable order that carries out the intended function of the procedure.

Further in accordance with the present invention, examples of types of "working apparatus" that may be inserted through the sterility barrier and into the sealed lumen of the elongate apparatus include imaging apparatus (e.g., intravascular ultrasound imaging apparatus), scopes (e.g., endoscopes, angioscopes), temperature sensors, pressure sensors, stylets (e.g., catheter tip-shaping stylets or stiffening stylets), light sources, light transmitting members (e.g., optical fibers or fiber optic bundles), magnets (e.g., permenant magnets or electromagnets), radiopaque markers, radiation collectors, an x-ray compass as described in U.S. Pat. No. 5,912,945 (DaSilva et al.), vibrating apparatus, ultrasonic apparatus, sonic apparatus, apparatus for delivery of ionizing radiation, apparatus for emitting energy, apparatus for absorbing energy, sensing apparatus, diagnostic apparatus or apparatus for rotational orientation of the catheter and/or longitudinal positioning of the catheter.

Further aspects of the present invention will become apparent to those of skill in the art upon reading and understanding of the examples and specific embodiments described in detail herebelow.

BRIEF DESCRIPTION OF THE DRAWINGS

FIG. 3a is an enlarged view of the distal end of the catheter device of FIG. 3.

FIG. 7a is an enlarged view of region 7a of FIG. 7.

FIG. 9 Is a longitudinal sectional view of a guide catheter that is useable for guiding various devices and specifically for delivering an deploying a radially expandable embolization member or blocker at a desired location within a blood vessel.

FIG. 9a is a side view of a pusher device that is useable to push a radially expandable occluder through the guide catheter device of FIG. 9.

FIG. 9b is a side view of a radially expandable occluder device that is useable in conjunction with the guide catheter or FIG. 9 and the pusher device of FIG. 9a.

FIG. 10 is a longitudinal sectional view of a catheter device of the present invention incorporating a detachable tubular sterility barrier.

FIG. 10a is an enlarged view of a portion of the device of FIG. 10.

DETAILED DESCRIPTION OF PREFERRED EMBODIMENTS

The following detailed description and the drawings to which it refers are provided for the purpose of describing and illustrating certain examples and presently preferred embodiments of the invention only, and not for the purpose of limiting the scope of the invention in any way.

A. The Basic Catheter Device

Figure 1:
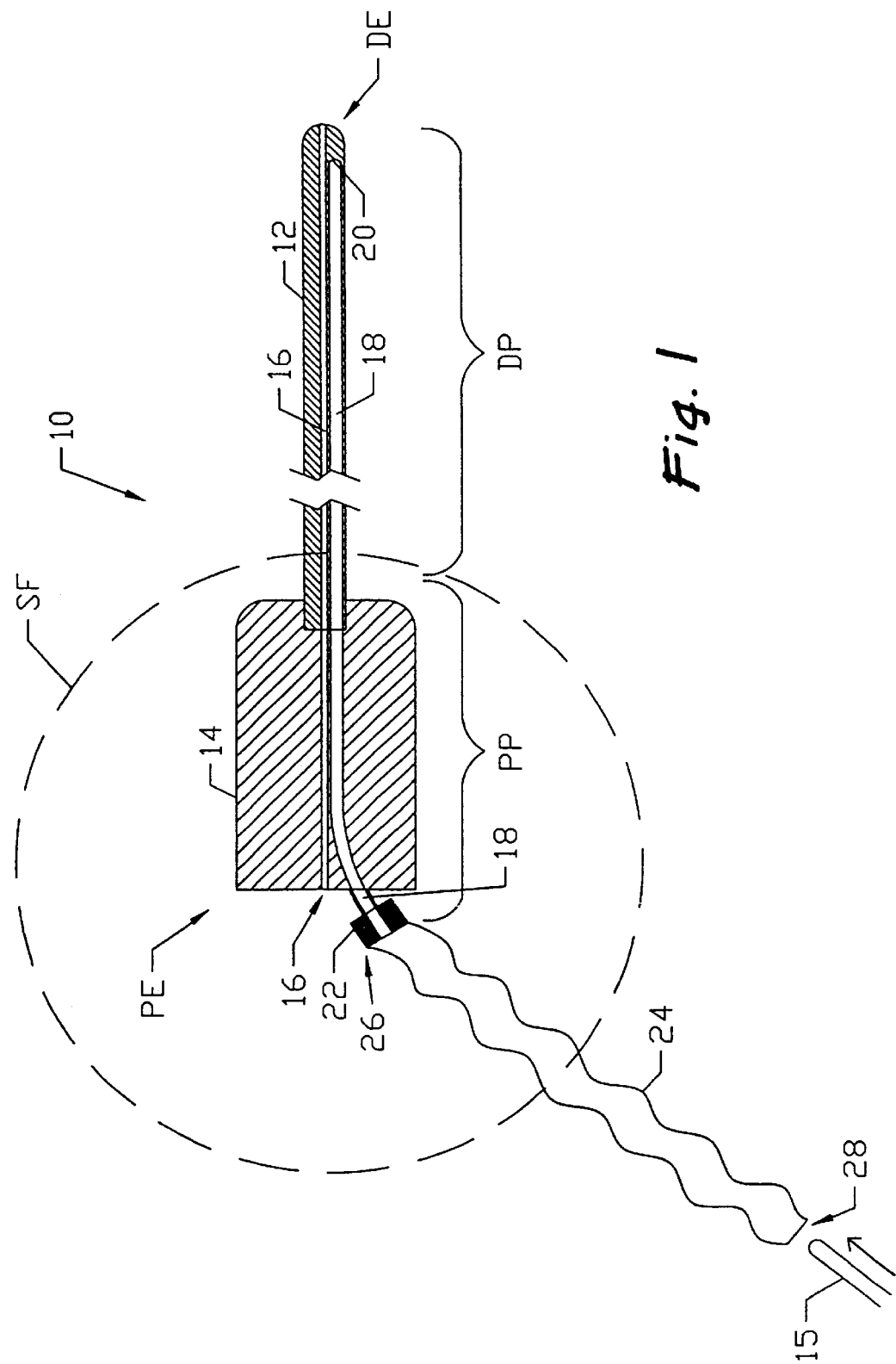
FIG. 1 is a longitudinal sectional view of a basic catheter device of the present invention.

A basic catheter device 10 of the present invention is shown in FIG. 1. This basic catheter device 10 comprises an elongate catheter body 12 attached to and extending distally from a hand piece 14. The catheter device 10 has a distal end DE and a proximal end PE. A through lumen 16 extends longitudinally through the catheter device from the proximal end PE through the distal end DE. Such through lumen 16 may be used for advancement of the catheter device over a previously inserted guidewire, for injection or infusion of fluids (e.g., medicaments, radiographic contrast agents, or for other purposes. A sealed lumen 18 extends longitudinally from the proximal end PE of the catheter device 10 and terminates distally in a closed end 20 located within the elongate catheter body 12. A proximal connector 22 is mounted on the hand piece 14 and the sealed lumen 18 of the device continues proximally through the connector 22 to facilitate insertion and advancement of an elongate apparatus (e.g., another catheter, a probe, a wire, a cable, a sensor, an imaging apparatus, an emitting apparatus, etc) through the connector 22 and into the sealed lumen 18 within the catheter body 12. An elongate, tubular sterility barrier 24 has a forward end 26 and a rearward end 28. The forward end 26 of the sterility barrier 24 is attached to the proximal connector 22 such that the sealed lumen 18 leads into the interior of the tubular sterility barrier 24.

In routine operation, a distal portion DP of the catheter body 12 is inserted into the patient's body while a proximal portion PP of the device 10 remains exteriorized. A sterile field SF is maintained around the proximal portion PP of the catheter device 10, as denoted by dotted lines on FIG. 1. The sterility barrier 24 extends through the sterile field SF such that the rearward end 28 of the sterility barrier 24 is located outside of the sterile field SF. The attachment between the forward end 26 of the sterility barrier 24 and proximal connector 22 is sufficiently sealed to prevent any microbes introduced within the interior of the sterility barrier 24 and/or within the interior of the sealed lumen 18 from escaping into the sterile field SF. Also, no openings are formed between the sealed lumen 18 the outer surface of the distal portion DP of the catheter body 12 such that, when the distal portion DP is inserted into a patients body, any microbes that the become introduced into the sealed lumen 18 will be contained within the catheter body 12 and will not escape into the patient's body.

Thus, in cases where the distal portion DP of the catheter body 12 has been inserted into the patient's body and the sterile field SF surrounding the proximal portion PP of the catheter device 10 has been established, a non-sterile working apparatus 15 may then be introduced into the rearward end 28 of the sterility barrier 24 then advanced through the tubular sterility barrier 24 and into the portion of the sealed lumen 18 located within the distal portion DP of the catheter body 12, without potential contamination of the sterile field SF or contamination of the patient's body. In other cases, it may be desirable to insert the non-sterile working apparatus through the sterility barrier 24 and into the sealed lumen 18 before the catheter device 10 is inserted into the body, and to subsequently insert the distal portion DP of the catheter body 12 into the patient while maintaining the rearward end 28 of the sterility barrier 24 outside of the sterile field SF thereby avoiding contamination of the sterile field by the portion of the non-sterile working apparatus 15 that protrudes out of the rearward end 28 of the sterility barrier 24. The present invention is useable in either of these ways.

One example of a clinical application of a catheter device 10 of this invention is to facilitate the repeated use of a working apparatus 15 that comprises a non-sterile intravascular ultrasound Imaging (IVUS) catheter for diagnostic or other coronary imaging. In this application, an antimicrobial solution (e.g., Betadine® brand povidone iodine, The Perdue Frederick Co., 100 Connecticut Avenue, Norwalk, Conn.) is applied to the patients skin in the area of the femoral artery and sterile drapes are applied to such area. Using sterile technique, a sterile introducer sheath is inserted percutaneously into the patient's femoral artery by a standard Seldinger introduction technique. Thereafter, a guidewire and a coronary artery guide catheter are inserted through the introducer sheath and advanced until the distal end of the guide catheter is located in the patient's right or left coronary ostium, as desired, and the guidewire extends through the lumen of the guide catheter and into the desired coronary artery. Thereafter, the proximal end of the guidewire is inserted into the distal end of the through lumen 16 of a sterile catheter device 10. The catheter device 10 is then advanced over the guidewire and through the coronary guide catheter until the distal end of the catheter device 10 is located in the desired coronary artery. This results in the distal portion DP of the catheter device 10 being located within the patient's body while the proximal portion PP of the catheter device 10 remains outside of the patient's body. A sterile field SF is maintained around the proximal portion PP of the catheter device 10 and the femoral entry site. The tubular sterility barrier 24 of the catheter device 10 is then arranged such that its rearward end 28 is located outside of the sterile field SF. A non-sterile working apparatus 15 comprising a reusable intravascular ultrasound imaging (IVUS) catheter or IVUS wire is then introduced, by a non-sterile operator, through the rearward end 28 of the sterility barrier 24 and into the interior of the tubular sterility barrier 24. The sterile operator then grasps the working apparatus 15 (e.g., the IVUS catheter or wire) through the flexible, sterile sterility barrier 24 and advances the working apparatus 15 (e.g., the, IVUS catheter or wire) into the sealed lumen 18 of the catheter device 10 to a position where the ultrasound transducer of the IVUS catheter or wire is located within the patient's coronary artery to be imaged. Prior to, during or after insertion of the IVUS catheter into the sealed lumen 18, the sealed lumen 18 may be substantially filled with a ultrasound transmissible material, such as saline solution or an ultrasound coupling lotion or gel (e.g., LiquaSonic Ultrasound Gel #001222, LiquaSonic Ultrasound Scanning Gel #001278 or LiquaSonic Ultrasound Lotion #001268, Chester Labs, Inc., 1900 Section Rd., Suite A, Cincinnati, Ohio 45237) to facilitate transmission of the ultrasound energy from the IVUS catheter through the catheter body 12. The sealed lumen may be evacuated by a large syringe or vacuum pump prior to or during introduction of the ultrasound transmissible material to avoid the formation of bubbles or air inclusions. The portion of the catheter body 12 surrounding the ultrasound transducer of the IVUS catheter or wire will be formed of material that is ultrasound-permeable so as to allow interrogating ultrasound from the ultrasound transducer to pass outwardly through the catheter body 12 and to allow reflected ultrasound to then pass inwardly through the catheter body 12 and be received by the ultrasound transducer of the IVUS catheter located within the sealed lumen 18. In this manner, the desired ultrasound image is obtained and displayed on a screen or monitor connected to the IVUS catheter. After the desired ultrasound image has been obtained, the IVUS catheter and the catheter device 10 are removed from the patients body. The sterile catheter device 10 is not reused and is disposed at the end of the procedure. The non-sterile IVUS catheter is, however, reuseable and may subsequently be reused in accordance with the foregoing methodology. In this manner, the expense of obtaining a new IVUS catheter for each procedure is avoided.

B. Tissue Penetrating Catheter Devices

Figure 2:
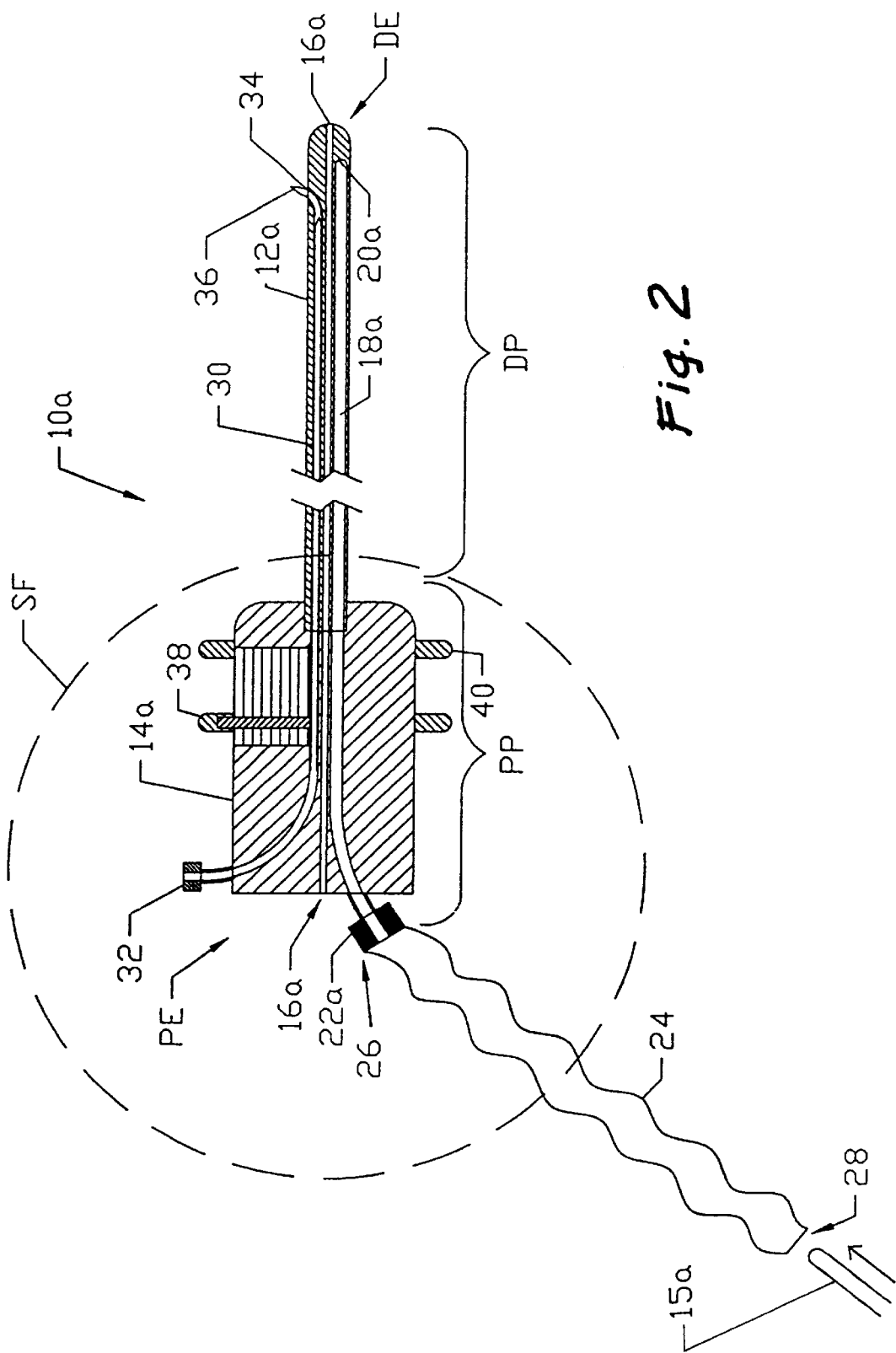
FIG. 2 is a longitudinal sectional view of a tissue penetrating catheter device of the present invention.
Figure 3:
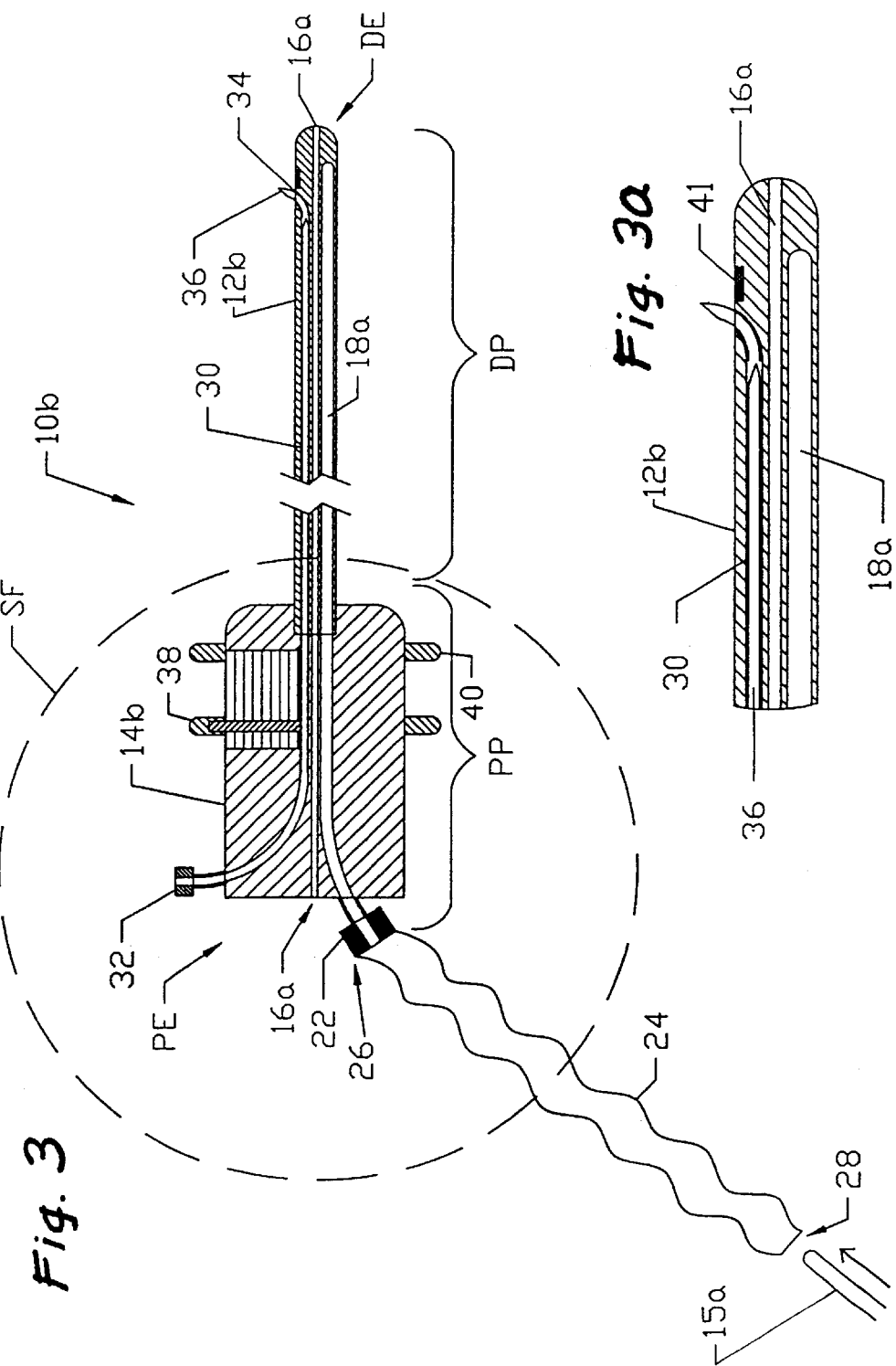
FIG. 3 is a longitudinal sectional view of a tissue penetrating catheter device of the present invention incorporating an orientation element to facilitate placement of the catheter to a desired rotational orientation within the body.

FIGS. 2–3a show examples of tissue penetrating catheter devices 10a, 10b of the present invention.

One tissue penetrating catheter device 10a of the present invention is shown in FIG. 2. This tissue penetrating catheter device 10a incorporates the elements of the basic catheter device 10 described hereabove, including an elongate catheter body 12a attached to and extending distally from a hand piece 14a, a through lumen 16a extending longitudinally through the catheter device 10a from its proximal end PE through the distal end DE, such through lumen 16a being useable for advancement of the catheter device 10a over a previously inserted guidewire, for injection or infusion of fluids (e.g., medicaments, radiographic contrast agents, saline solution, etc.) or for other purposes. Also, as in the basic catheter 10, a sealed lumen 18a extends longitudinally from the proximal end PE of the catheter device 10a and terminates distally in a closed end 20a located within the elongate catheter body 12a. In embodiments where the sealed lumen 18a is used to receive a working apparatus 15a that comprises an ultrasound imaging device, a quantity of liquid (e.g., saline solution), coupling gel, or other ultrasound transmission medium may be placed in the sealed lumen 18a concurrently with or prior to the advancement of the working apparatus 15a comprising an ultrasound imaging apparatus thereinto to thereby eliminate gas filled voids that may interfere with passage of the ultrasound and to facilitate ultrasound imaging of anatomical structures located adjacent to the distal portion DP of the catheter body 12a. Also, in embodiments where the working apparatus 15a inserted into the sealed lumen 18a is used for imaging, at least the portion of the catheter body 12a through which an image is to be obtained will be formed of material that may be permeated by the form of energy (e.g., ultrasound) that is emitted and/or received by such working apparatus 15a to accomplish the desired imaging. A proximal connector 22a is mounted on the hand piece 14a and the sealed lumen 18a of the device 10a continues proximally through the connector 22a to facilitate insertion and advancement of an elongate apparatus (e.g., another catheter, a probe, a wire, a cable, a sensor, an imaging apparatus, an emitting apparatus, etc)through the connector 22a and into the sealed lumen 18a within the catheter body 12a. Also, as in the basic catheter device 10, this tissue penetrating catheter device 10a has an elongate, tubular sterility barrier 24, the forward end 26 of which is attached to the proximal connector 22a such that the sealed lumen 18a leads into the interior of the tubular sterility barrier 24.

This tissue penetrating catheter device 10a also incorporates elements that are not included in the basic catheter device 10 described above. For example, a penetrator lumen 30 is formed in and extends generally longitudinally through the catheter, body 12a, through the hand piece 14a and through a penetrator port 32 mounted on the hand piece 14a. This penetrator lumen 30 terminates distally in a penetrator outlet aperture 34 and a penetrator 36 having a sharp distal tip is slidably disposed within the penetrator lumen 30. The penetrator 36 is connected to a penetrator advancement/retraction knob 38 formed on the hand piece 14a. When the penetrator advancement/retraction knob 38 is in its retracted position as shown in FIG. 2, the penetrator 36 will be retracted fully within the penetrator lumen 30. When the penetrator advancement/retraction knob 38 is advanced toward its stop member 40 a distal portion of the penetrator will advance out of the penetrator outlet aperture 34 and laterally from the catheter body 12a as shown in dotted lined in FIG. 2. In this manner, the penetrator 36 may be used to penetrate outwardly through the wall of a blood vessel or other anatomical structure in which the distal portion DP of the catheter body 12a is positioned and to another blood vessel or other target location within the patient's body. A lumen extends longitudinally through the penetrator 36 such that a guide wire (not shown) may be inserted into the penetrator port 32, through the lumen of the penetrator 36 and out of its distal end. To facilitate proper positioning of the catheter body 12a and precise aiming of the penetrator 36 before its advancement, a working apparatus 15a that comprises an imaging apparatus (such as an IVUS catheter) may be advanced into the sealed lumen 18a and used to image the blood vessel or other anatomical structure in which the distal portion DP of the catheter body 12a is positioned, the other blood vessel or other target location to which the penetrator 36 is intended to pass and/or portions of the catheter device 10a itself. Further details about the construction, operation, aiming and deployment of the penetrator 36, as well as detailed descriptions of clinical procedures that may be performed with this tissue penetrating catheter device 10a are found in U.S. Pat. Nos. 5,830,222 and 6,283,951, the entire disclosures of which are hereby expressly incorporated herein by reference.

Generally speaking, in routine operation, a distal portion DP of the catheter body 12a may be inserted into the patient's body by the same technique described hereabove with respect to the basic catheter 10, such that a proximal portion PP of the device 10a remains outside the patient's body and a sterile field SF is established around the proximal portion PP of the device 10a, as denoted by dotted lines on FIG. 2. The sterility barrier 24 is arranged such that it extends through the sterile field SF with its rearward end 28 located outside of the sterile field SF. After the distal portion DP of the catheter body 12a has been inserted into the patient's body and the sterile field SF surrounding the proximal portion PP of the catheter device 10a has been established, a non-sterile working apparatus 15a such as an intravascular ultrasound imaging (IVUS) catheter may be introduced into the rearward end 28 of the sterility barrier 24 then advanced through the tubular sterility barrier 24 and into the portion of the sealed lumen 18a located within the distal portion DP of the catheter body 12a, without potential contamination of the sterile field SF or contamination of the patient's body. The non-sterile, working apparatus 15a may then be used to perform its desired function and may be removed, re-inserted, replaced, rotated or repositioned at will without disturbing the placement and positioning of the tissue penetrating catheter device 10a. In applications where the non-sterile working apparatus 15a comprises an imaging device such as an intravascular ultrasound imaging (IVUS) catheter, it may be used to image the anatomy surrounding or near the distal portion DP of the catheter device 10a and/or portions of the catheter device 10a itself, to aim the penetrator 36 at the desired target before the penetrator is advanced from the catheter body 12a. In this regard, it is desirable for the operator to have some indication of the trajectory or path that will be followed by the penetrator 36 when the penetrator 36 is subsequently advanced from the catheter body 12a. In the embodiment shown in FIG. 2, this indication of the trajectory or path that will be followed by the penetrator 36 may be obtained by anchoring or mechanically keying the working apparatus 15a such that it is held in a known rotational orientation within the sealed lumen 18a such that a particular location on the image generated by the working apparatus 15a will correspond to the location to which the distal tip of the penetrator 36 will extend when the penetrator 36 is advanced. For example, a 360 degree phased array ultrasound transducer may be incorporated into the working apparatus 15a and used to produce the image and the working apparatus 15a may be anchored in a fixed rotational position within the sealed lumen 18a such that a particular element on the phased array transducer is associated with the radial location of the penetrator outlet aperture 34 or the radial location at which the penetrator tip will arrive when it is fully advanced. This key element of the phased array transducer may be in a known location on the image monitor or a discrete marking, such as a line, may appear on the image monitor to indicate the radial position of that particular element of the transducer. In this manner, the operator may then position and rotationally orient the catheter device 10a within the patient's body such that the key element of the ultrasound transducer is radially aligned with the target location to which the penetrator 36 is desired to penetrate. This radial alignment of the key transducer element with the target location ensures that when the penetrator 36 is subsequently advanced from the catheter body 12a, it will enter the target location. Thus, after the catheter device 10a has been placed in such position and rotational orientation within the patient's body and the operator has verified that the key transducer element is radially aligned with the target location, the operator may advance the penetrator advancement/retraction knob 38 in the distal direction until it reaches the penetrator stop member 40, thereby causing the penetrator 36 to become fully advanced from the catheter body 12a, through the wall of the blood vessel or other anatomical structure in which the catheter body 12a is positioned, and to the target location within the patient's body. Thereafter, a guidewire may be advanced through the penetrator port 32, through the lumen of the penetrator 36 and into the target location. Therafter, the operator may move the penetrator advancement/retraction knob 38 proximally to its original position, thereby retracting the penetrator 36 into the catheter body 12a while allowing the guidewire that was inserted through the lumen of the penetrator 36 to remain extended into the target location.

As shown in FIGS. 3 and 3a, as an alternative to rotational locking (e.g., mechanical keying) or anchoring of the working apparatus 15a within the sealed lumen 18a, an orientation element 41, such as an imageable marker, may be associated with the catheter device 10b to facilitate the aiming of the penetrator 36 toward the target location. In this regard, FIGS. 3 and 3a show an embodiment of a tissue penetrating catheter 10b that has all of the same elements as the tissue penetrating catheter device of FIG. 2 but additionally an orientation element 41 formed on the catheter device 10b. The various types, structures and modes of operation of the orientation element are described in detail in U.S. Pat. Nos. 5,830,222 and 6,283,951, such disclosures being expressly incorporated herein by reference.

The orientation element 41 may be a marker that is imageable by the working apparatus 15a and may be formed integrally with or mounted on the distal end of the catheter body 12b, as shown in FIGS. 3 and 3a.

C. Treatment Catheter Devices

Figure 4:
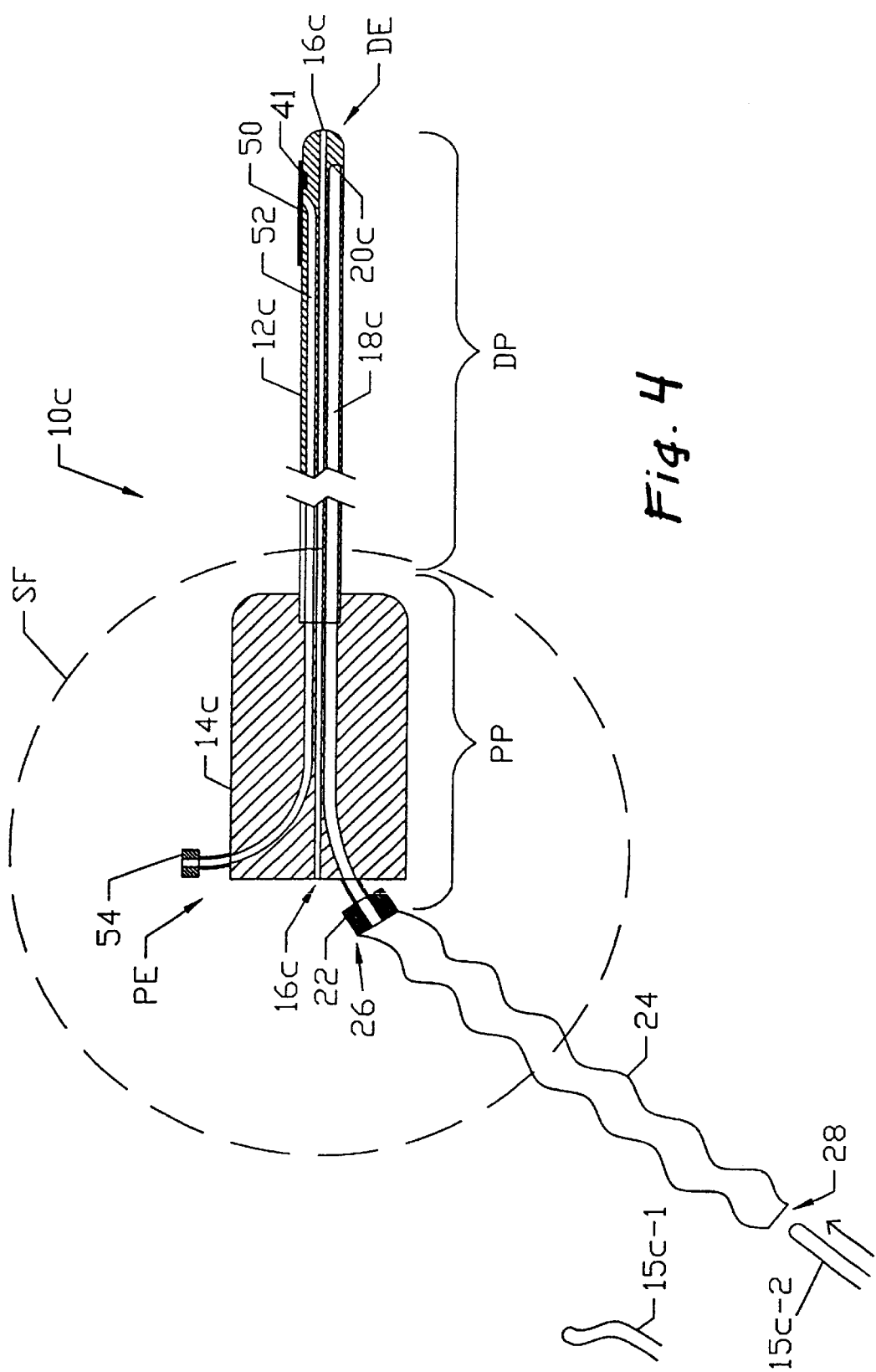
FIG. 4 is a longitudinal sectional view of a catheter device of the present invention incorporating a treatment element for delivering a therapeutic treatment and an orientation element to facilitate placement of the catheter in a desired position and rotational orientation within the body.

The present invention includes various treatment catheter devices 10c capable of delivering a flow of energy, radiation, infusion of a drug or other therapeutic substance or other treatment to a site located within the patient's body. An example of one such treatment catheter device is shown in FIG. 4. This treatment catheter device 10c incorporates all of the same elements as the basic catheter device 10 described above, including an elongate catheter body 12c, a hand piece 14c, a through-lumen 16c that extends longitudinally from the proximal end of the hand piece 14c to the distal end DE of the catheter body 12c and a sealed lumen 18c that extends from a connector 22 mounted on the hand piece 14c, through the hand piece 14c and longitudinally through the catheter body 12c to a closed distal end 20c.

A treatment element 50 is located on the distal portion DP of the catheter body 12c that becomes inserted into the patient's body. This treatment element 50 may comprise an electrode, radiation emitter, lamp, lens through which light may pass, porous balloon, infusion port or any apparatus or opening capable of directing or transferring a flow of energy (e.g., electrical current, ionizing radiation, ultraviolet light, white light, etc), a flow of liquid, or other treatment modality through the side of the catheter body 12c to a target location on or adjacent to the wall of the blood vessel or other anatomical conduit in which the distal portion DP of the catheter body 12c is positioned. Wire(s), optical fiber(s), cable(s) or other connector(s) may extend through a lumen 52 that runs through catheter device 10c from a treatment connector 54 formed on the hand piece 14c to the treatment element 50.

In routine operation, the distal portion DP of the treatment catheter device 10c is positioned within the body of the patient and a sterile field SF is established around the proximal portion PP of the catheter device 10c and the entry site where the catheter body 12c enters the body of the paient, in accordance with the procedure described hereabove. Also as described hereabove, the sterility barrier 24 is arranged such that its rearward end 28 is positioned outside of the sterile field SF. One or more non-sterile, elongate working apparatus 15c-1, 15c-2 is/are insertable into the rearward end 28 of sterility barrier 24, and advanceable through the proximal connector 22 and into the sealed lumen 18c within the distal portion DP of the catheter body 12c. Thereafter, each such non-sterile, elongate working apparatus 15c-1, 15c-2 is used to perform some desired function associated with delivery of the treatment via the treatment element 50. For example, the working apparatus may comprise an imaging device, such as an intravascular ultrasound imaging (IVUS) catheter, and such imaging device may be utilized from a location within the sealed lumen 18c to image the adjacent anatomy of the patient and to guide the positioning and rotational orientation of the catheter to ensure that the treatment element 50 is properly positioned to deliver the desired treatment to the desired tissues or anatomical structures. Optionally, this treatment catheter device 10c may also incorporate an orientation element 41 of the type shown in FIGS. 3 and 3a and described hereabove, to facilitate rotational orientation of the catheter body 12c within the blood vessel or other anatomical structure such that the treatment element 50 is properly positioned to deliver its treatment to the desired blood vessel wall, tissue, tumor or other anatomical structure. Irrespective of whether an orientation element 41 is included, after the imaging device has been utilized to guide and/or verify the proper positioning of the treatment element 50, a treatment delivering apparatus (not shown) such as an electrical signal generator, ultraviolet light source, white light source, or other suitable apparatus may be connected to the treatment connector 54 and used to deliver the desired form of energy (e.g. electrical current, ultraviolet light, white light, heat, cold, etc.) through the treatment lumen 52 to the treatment element 50. The treatment element 50 then disseminates or delivers the desired treatment to the desired tissue or anatomical structure.

One specific example of a clinical application of the treatment catheter 10c is for the delivery of light energy (e.g., UV light, laser light) to a specific area (e.g., within a tumor, upon the luminal surface of a blood vessel, etc) for the purpose of causing photo-activation of a drug or chemical agent (e.g., a chromophore) or to effect photodynamic therapy (PDT). In PDT a photosensitizing agent is administered, usually intravenously, to the patient and, after the photosensitizing agent has been taken up by cancer cells, a laser light of a specific wavelength is shone on the area of the cancer cells to produce a photochemical reaction that destroys the cancer cells. One such photosensitizing agent is known as Photofrin II. In addition to Photofrin II, a number of new synthetic photosensitizing agents are under development. Due to improved penetration and/or decreased side effects (such as untoward skin sensitivity to sunlight), dosing with these newer synthetic agents may be repeated more frequently than the single shot therapy currently offered with Photofrin. PDT may be useable for the treatment of mesothelioma, locally advanced lung cancer with a malignant pleural effusion, recurrent pleural effusions from a variety of cancers, and cancers that have seeded the abdominal cavity, including carcinomas, sarcomas and ovarian cancers. At present, it is typically necessary for the laser light to be applied to the area of the cancer cells through an open surgical incision. However, the treatment catheter device 10c could be used to effect less invasive administration of the laser light to the affected area by advancing the catheter body 12c through blood vessels, the GI tract, the genitourinary tract, the respiratory tract (e.g., the catheter body could be a bronchoscope), or into a body cavity through a laparoscopy or thoracoscopic portal, etc. to position the treatment apparatus 50 (e.g., a window or lens for outlet of the laser light) adjacent the cancerous area.

By way of example only, in a treatment catheter device 10c adapted for use in PDT for treatment of ovarian cancer, the treatment element 50 will comprise a lens or window through which laser light of the desired wavelength may be passed and a fiber optic for transmission of such laser light will extend through the treatment lumen 52 for transmission of the laser light to the lens or window. Also, two (2) separate working apparatus 15c-1 and 15c-2 will be used during different stages of the procedure. The first working apparatus 15c-1 comprises a curved stylet that causes shaping of the distal portion of the catheter body 12c to facilitate its advancement through the tortuous genitourinary tract and into the affected ovary. The second working apparatus 15c-2 comprises an ultrasound imaging catheter that is useable to image the area around the distal portion of the catheter body 12c to guide and verify proper placement of the treatment apparatus 50 prior to delivery of the laser light and/or to guide movement of the treatment apparatus 50 during delivery of the laser light to spread the laser light over the entire area in which the cancer cells are present.

A photosensitizing agent is administered to the patient intravenously a predetermined time (e.g., 5 days) prior to the laser procedure. The patient's pelvic area will be prepared and covered with sterile drapes, establishing a sterile field SF. The catheter device 10c is positioned within the sterile field SF and the sterility barrier 24 is arranged such that its rearward end 28 is disposed outside of the sterile field SF. The first working apparatus 15c-1 is a resilient stylet that is preformed to a curved configuration as shown in FIG. 4. This first working apparatus 15c is introduced through the rearward end 28 of the sterility barrier 24 and is advanced into the sealed lumen 18c until its distal end reaches the closed distal end 20c of the sealed lumen 18c. In this manner, the insertion of the curved stylet will cause the distal portion of the catheter body 12c to assume a curved shape that corresponds to the shape of the stylet. This curved shape has been predetermined to be a shape that will facilitate entry and advancement of the catheter body distal portion DP into the desired fallopian tube adjacent to the desired ovary. Accordingly, with the curved stylet so inserted, the distal portion DP of the catheter body will be inserted transvaginally through the uterus and into the desired fallopian tube. After the distal portion DP of the catheter body 12c has entered the desired fallopian tube the first working apparatus 15c-1 will be retracted and removed. The second working apparatus 15c-2 comprising an ultrasound imaging device is then introduced through the rearward end 28 of the sterility barrier 24, is grasped through the sterility barrier 24 by the operator's hand and is advanced into the sealed lumen 18c. This ultrasound imaging device is actuated and used to obtain a 360 degree ultrasound image on a screen or monitor that is visible to the operator. The operator then uses this image to guide the longitudinal positioning and rotational orientation of the distal portion DP of the catheter body 12c such that the treatment element 50 is positioned immediately adjacent to the ovarian tumor. A laser generating instrument is then connected to connector 54 and is utilized to pass laser light of the desired wavelength through the optical fiber disposed within the treatment lumen 52 and outwardly through the window or lens comprising the treatment element 50. Such laser energy then enters the ovarian tumor and destroys cancer cells that contain the photosensitizing agent while causing minimal damage to noncancerous cells that contain less concentration or no concentration of the photosensitizing agent.

Another example of a possible application of the treatment catheter device 10c is for the delivery of radiation to the wall of a blood vessel or other treatment site that is desired to be irradiated. In this application, the first working apparatus 15c-1 comprises an intravascular ultrasound imaging (IVUS) catheter that would not necessarily have a curved configuration as shown in the first working apparatus 15c-1 described above and shown in FIG. 4. The second working apparatus 15c-2 comprises a radiation emission source for delivery to the treatment element 50 of the desired form of ionizing radiation that is to be delivered to the blood vessel wall or other location. In this example, the treatment element 50 is a radiation outlet port or window through which ultrasound from the first working apparatus 15c-1 and radiation from the second working apparatus 15c-2 may selectively pass, while the remaining portions of the catheter body 12c remain shielded so as to prevent the transmission of the ultrasound or radiation therethrough. A sterile field SF is established and the distal portion DP of the catheter body 12c is inserted into a blood vessel of the patient in the manner described hereabove. Prior to or after insertion of the distal portion DP of the catheter body 12c into the patient's body, the first working apparatus 15c-1 comprising the IVUS device is inserted through the rearward end 28 of sterility barrier 24 and is grasped by the operator's hand through the sterility barrier 24 and advanced into the sealed lumen 18c to a position where the transducer of the IVUS device obtains an image through the window of the treatment element 50. The image obtained through the IVUS device is then used to guide the longitudinal positioning and rotational orientation of the distal portion DP of the catheter body 12c such that the treatment element 50 becomes positioned immediately adjacent the portion of the blood vessel wall or other anatomical structure to be irradiated. After the proper positioning of the treatment element 50 has been verified, the operator once again grasps the first working apparatus 15c-1 through the sterility barrier 24 and retracts the first working apparatus 15c-1 in the proximal direction causing that working apparatus 15c-1 to be removed from the catheter device 10c out of the rearward end 28 of the sterility barrier 24. Thereafter, the second working device 15c-2 comprising the radiation source (e.g., radiation emitter) is passed through the distal end 28 of the sterility barrier 24 and is advanced into the sealed lumen 18c until it abuts against the closed distal end 20c of the sealed lumen. When so positioned, the radiation source will cause radiation to pass outwardly through the treatment element 50. The radiation source will be maintained in such position for a period of time sufficient to deliver the desired radiation treatment to the blood vessel wall or other anatomical location. Thereafter, the radiation source and the catheter device 10c will be removed from the patient's body.

Figure 5:
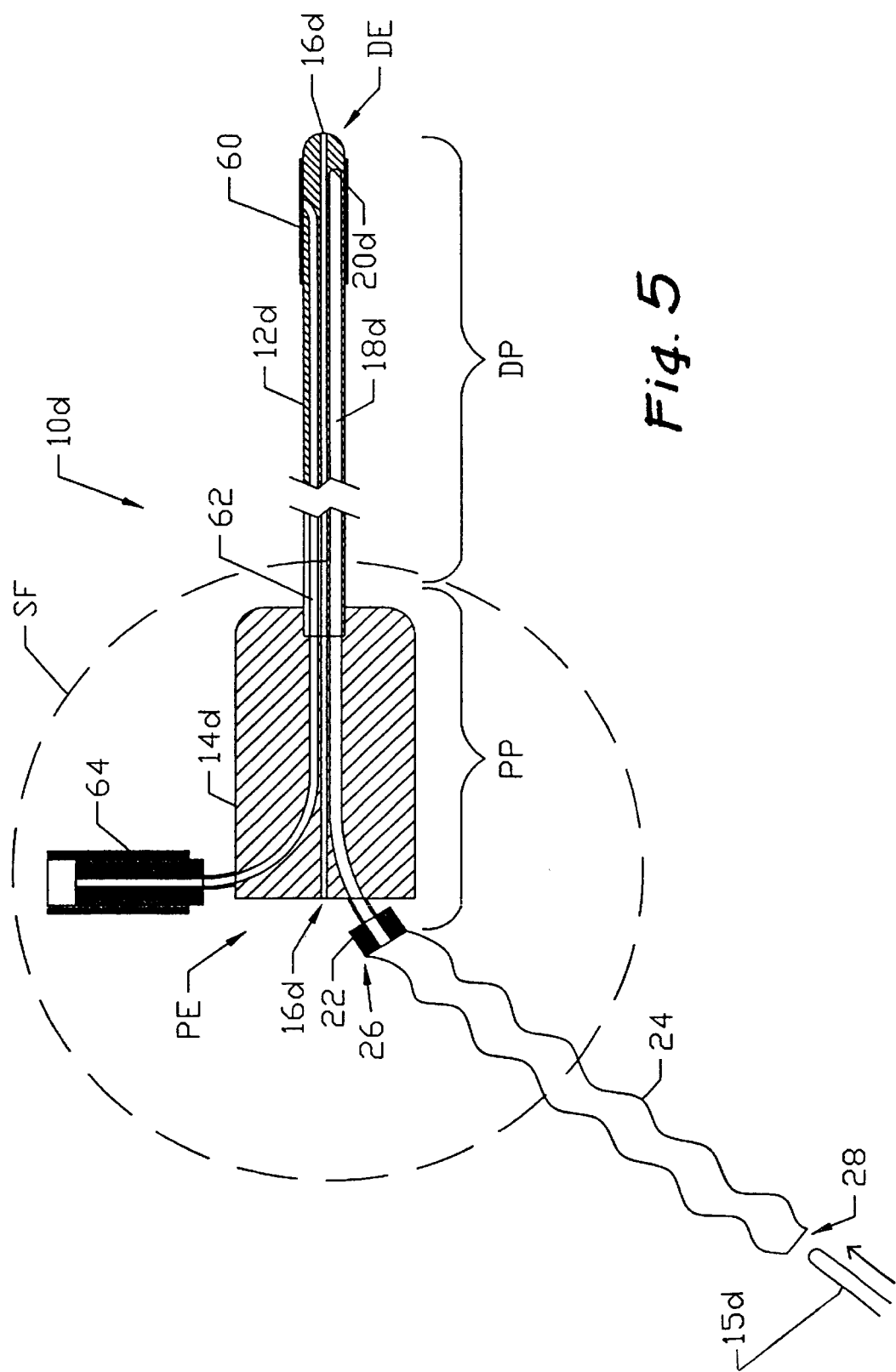
FIG. 5 is a longitudinal sectional view of a catheter device of the present invention useable for delivering a radially expandable apparatus such as connector, stent or stented graft.

D. Catheter Device for Delivery of Radially Expandable Stents, Connectors and Stented Grafts FIG. 5 shows a delivery catheter device 10d for delivering stents, connectors, stented grafts, anastomotic clips, other clips, connectors (e.g., the clips and connectors described in PCT International Publication Nos. WO97/278898 and WO99/25273) or other radially expandable implantable apparatus within the body. This delivery catheter device 10d incorporates all of the elements of the above-described basic catheter device 10, including an elongate catheter body 12d, a hand piece 14d, a through-lumen 16d that extends longitudinally from the proximal end of the hand piece 14d to the distal end DE of the catheter body 12d and a sealed lumen 18d that extends from a connector 22 mounted on the hand piece 14d, through the hand piece 14d and longitudinally through the catheter body 12d to a closed distal end to 20d.

A radially expandable balloon 60 is mounted on the catheter body 12d at a location on its distal portion DP that becomes inserted into the body of the patient. The balloon inflation lumen 62 extends through the catheter device 10d from an inflation port located on the proximal connector 14d to an opening into the interior of the balloon. A pump 64 is attached to the balloon inflation port to pump pressurized inflation fluid through the balloon inflation lumen 62 into the balloon thereby causing radial expansion of the balloon. A plastically deformable stent, stented graft, connector or other radially expandable implantable apparatus is mounted on the deflated balloon such that when the balloon is inflated, the stent, stented graft, connector or other radially expandable implantable apparatus will be caused to radially expand and to plastically deform to its radially expanded configuration.

As discussed above, it may be desirable to carry out intraluminal ultrasound imaging of the blood vessel or other anatomical structure in which the distal portion of the catheter body 12d is positioned prior to, during or after radial expansion and implantation of the stent, stented graft, connector or other radially expandable implantable apparatus. Thus, a working apparatus 15d comprising an intravascular ultrasound imaging (IVUS) catheter may be inserted into the sterility barrier 24 and advanced into the sealed lumen 18d to accomplish ultrasound imaging. As described hereabove, the rearward end 28 of the sterility barrier 24 will be positioned outside of the sterile field SF and the IVUS catheter inserted through the sterility barrier may be non-sterile. In this manner, the IVUS catheter may be reused on a number of patients without requiring sterilization between patients.

It will be further appreciated that more than one non-sterile working apparatus 15d may be alternately inserted into the sealed lumen 16d. For example, in procedures where a stent is implanted in a blood vessel to treat an atherosclerotic occlusion of the blood vessel, it may be desirable to administer a dose of ionizing radiation to the wall of the blood vessel in the area where the stent has been implanted to deter or prevent subsequent reocclusion of the blood vessel. In this regard, after the IVUS catheter has been removed from the sealed lumen 18d and from the interior of the sterility barrier 24, a second working apparatus comprising an elongate member having a source of ionizing radiation mounted thereon or therein may be advanced into the rearward end 28 of the sterility barrier 24, through the interior of the sterility barrier 24 and into the sealed lumen 18d to a position where the source of ionizing radiation is located adjacent to the region of the blood vessel within which the stent has been implanted. The source of ionizing radiation will then be allowed to remain in that position for a period of time that has been calculated to deliver the desired dose of ionizing radiation to the blood vessel wall. Thereafter, the second working apparatus 15d comprising the source of ionizing radiation may be withdrawn and removed. Because the sterility barrier 24 and sealed lumen 18d prevent microbial contamination of the sterile field SF and/or the patient, it is possible to reuse the second working apparatus 15d without requiring that it be sterilized. The ability to reuse the radiation source is advantageous in view of the expense associated with the purchase of radioactive materials and the difficulty associated with their disposal. Furthermore, the ability to reuse the radiation source without sterilization is advantageous in view the fact that handling and sterilization of a radioactive source can be complicated due to the need for maintaining shielding of the radioactive source during the sterilization procedure.

It will be appreciated by those skilled in the art that not all stents, stented grafts, connectors, clips, anastomotic clips and other radially expandable implantable apparatus are plastically deformable and capable of being radially expanded by a balloon in the manner described above. Indeed, various self-expanding stents, stented grafts, connectors and other radially expandable implantable apparatus are well-known. Self expanding apparatus of this type are typically formed of resilient material and are biased to their radially expanded configurations. Such self expanding apparatus are typically mounted on a delivery catheter, compressed to a radially collapsed configuration and maintained in such radially collapsed configuration by way of a sheath or other constraining member. When it is desired to release the apparatus for radial self-expansion and implantation, the sheath or constraining member is retracted thereby allowing the apparatus to radially expand and become implanted. The catheter device 10d described above may be modified for delivery and deployment of such self expanding apparatus by eliminating the balloon, balloon inflation lumen 62 and pump 64 and replacing such elements with a sheath or retainer that will constrain or hold the self-expanding apparatus in a radially collapsed position on the catheter body 12d and a mechanism for retracting or moving the sheath or retainer so as to release the self expanding apparatus, when desired.

E. Balloon Angioplasty Catheter Device

Figure 6:
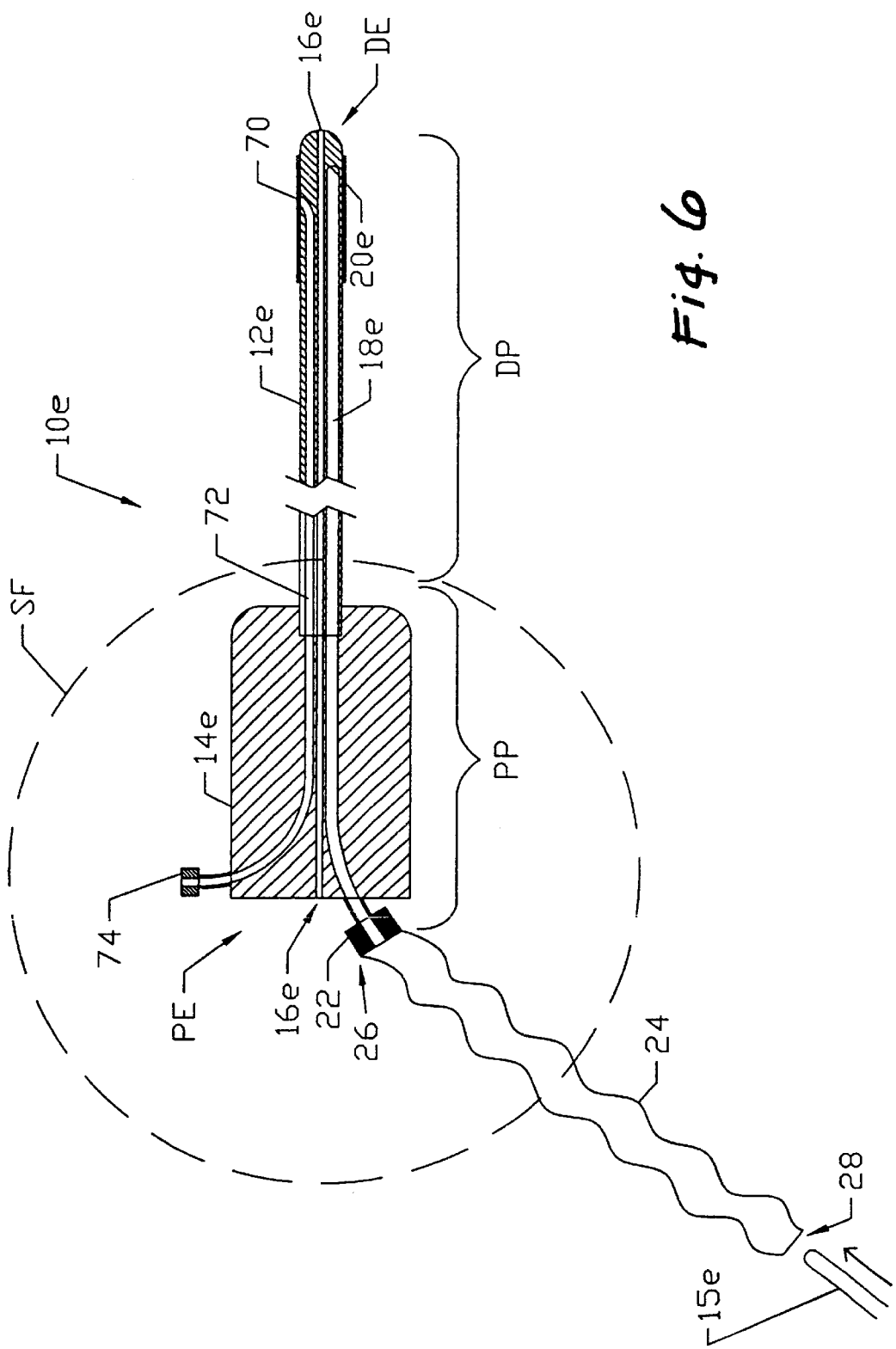
FIG. 6 is a longitudinal sectional view of a balloon angioplasty catheter device of the present invention.

FIG. 6 shows an example of a balloon angioplasty catheter device 10e of the present invention. This balloon angioplasty catheter device 10e incorporates all of the same elements as the basic catheter device 10 described above, including an elongate catheter body 12e, a hand piece 14e, a through-lumen 16e that extends longitudinally from the proximal end of the hand piece 14e to the distal end DE of the catheter body 12e and a sealed lumen 18e that extends from a connector 22 mounted on the hand piece 14e, through the hand piece 14e and longitudinally through the catheter body 12e to a closed distal end 20e.

Additionally, a radially expandable angioplasty balloon 70 is mounted on the distal portion DP of the catheter body 12e. The balloon inflation lumen 72 extends from a balloon inflation connector 74 located on the hand piece 14e, through the hand piece 14e, through the catheter body 12e and into the interior inflation space of the balloon 70.

In routine operation, the distal portion DP of the balloon angioplasty catheter device 10e is positioned within the body of the patient and a sterile field SF is established around the proximal portion PP of the catheter device 10e and the entry site where the catheter body 12e enters the body of the patient, in accordance with the procedure described hereabove. Also as described hereabove, the sterility barrier 24 is arranged such that its rearward end 28 is positioned outside of the sterile field SF. Thereafter, a working apparatus 15e useable to perform some desired function associated with the delivery of the balloon angioplasty treatment is inserted through the sterility barrier 28 and into the sealed lumen 18e. For example, the working apparatus 15e may comprise an imaging device, such as an intravascular ultrasound imaging (IVUS) catheter, and such imaging device may be utilized from a location within the sealed lumen 18e to image the adjacent anatomy of the patient and to guide the positioning of the balloon 70 prior to, during or after its inflation. In this manner the IVUS may be used to ensure that the balloon 70 is properly positioned to treat the atherosclerotic obstruction of the blood vessel, or to observe the inflation of the balloon to ensure that it is not over-inflated or under-inflated, or to verify that the desired lumen size of the vessel has been created by the angioplasty procedure, or for other reasons.

After the imaging device has been utilized to guide and/or verify the proper positioning of the balloon 70, the working apparatus 15e may be removed from the device 10e. Alternatively or additionally, a working apparatus 15e comprising a source of ionizing radiation may be inserted through the sterility barrier and into the sealed lumen 12e to deliver a radiation treatment to the wall of the blood vessel treated by the balloon angioplasty, in the same manner described hereabove in reference to stent placement.

F. Atherectomy Catheter Device

Figure 7:
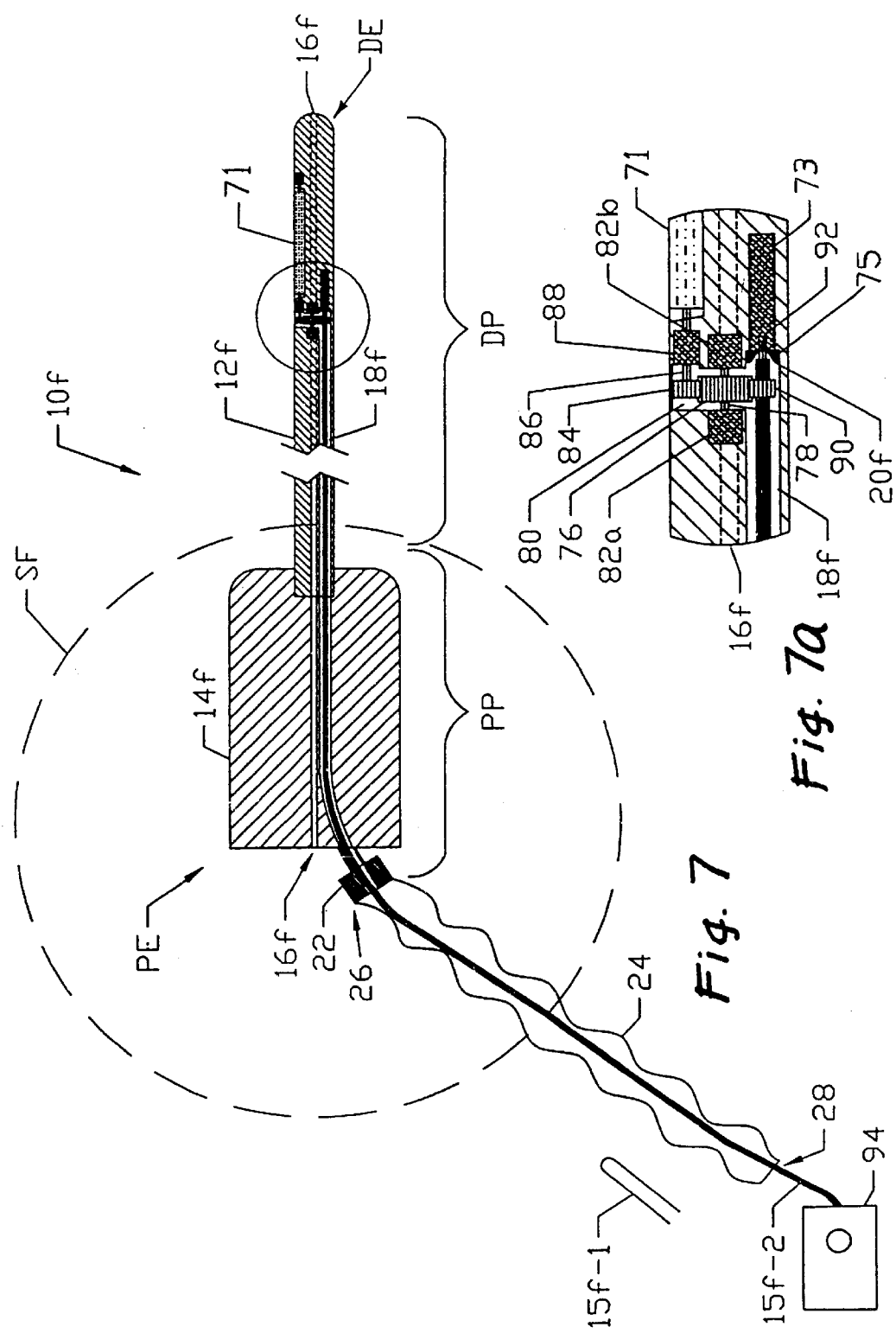
FIG. 7 is a longitudinal sectional view of a side-cutting atherectomy catheter device of the present invention.

FIGS. 7 and 7a show one example of an atherectomy catheter device 10f of the present invention wherein the non-sterile working apparatus 15f-1 and/or 15f-2 may comprise a rotating drive shaft that is used to drive an atherectomy cutter 70 and/or an imaging apparatus such as an intravascular ultrasound (IVUS) catheter or wire useable to image the surrounding blood vessel wall and adjacent anatomy. As shown, this atherectomy catheter device 10f shares a number of common elements with the above-described basic catheter device 10 including an elongate catheter body 12f, a hand piece 14f, a through-lumen 16f that extends longitudinally from the proximal end of the hand piece 14f to the distal end DE of the catheter body 12f and a sealed lumen 18f that extends from a connector 22 mounted on the hand piece 14f, through the hand piece 14f and longitudinally through the catheter body 12f to a closed end 20f.

A thrust bearing 73 is mounted within the catheter body 12f at the closed distal end 20f of the sealed lumen 18f and a concave, rotatable idler member 75 is rotatably connected to the thrust bearing 73 and mounted within the distal end 20f of the sealed lumen 18f. A central gear 76 having a hollow axle 78 is positioned within a sealed cavity 80 that is located immediately adjacent to, and opens into, the sealed lumen 18f. The opposite ends of the hollow axle 78 of the central gear 76 are inserted into hollow bearings 82a and 82b mounted proximal and distal to the central region of the sealed cavity 80, as shown. Another gear 84 has at axle 86 that extends through bearing 88 and is rigidly connected to the atheterectomy cutter 70 so as to rotatably drive the atherectomy cutter 71. As described more fully herebelow, one of the non-sterile working apparatus 15f-2 comprises an elongate flexible drive shaft having a gear 90 mounted coaxially thereon at a location near its distal end 92. The distal tip 92 of the drive shaft is tapered and configured to seat within and engage the concave, rotatable idler member 75 such that rotation of the dive shaft will cause concurrent rotation of the idler 75 within its bearing 72. The provision of the idler 75 and thrust bearing 73 will allow high speed rotation of the drive shaft with minimal friction. In some embodiments the idler 75 and bearing 72 may be unnecessary.

In typical operation, the atherectomy catheter device 10f is inserted into the patient's body, using the above-described sterile insertion technique, such that a distal portion DP of the catheter body 12f is within patient's body and a proximal portion PP remains located outside the patient's body. A sterile field SF is thus established and maintained around the proximal portion PP of the device 10f and around the site at which the device 10f enters the patient's body. The tubular sterility barrier 24 is arranged such that its rearward end 28 is located outside of the sterile field SF. An ultrasound coupling lotion or gel is placed in the sealed lumen, free of bubbles or air inclusions, as described above. Thereafter, prior to or after insertion of the catheter device 10f first non-sterile, elongate working apparatus 15f-1 comprising an intravascular ultrasound imaging apparatus (IVUS) is inserted into the rearward end 28 of the sterility barrier 24, and is advanced through the proximal connector 22 and into the sealed lumen 18f within the distal portion DP of the catheter body 12f. Thereafter, the atherectomy catheter device 10f is advanced through the patient's vasculature and the first non-sterile, elongate working apparatus 15f-1 is used to guide the longitudinal placement and rotational orientation of the atherectomy cutter 71 at the site of the obstructive matter to be removed. After the atherectomy catheter device 10f has been so positioned, the first non-sterile working apparatus 15f-1 comprising the IVUS device is removed and a second non-sterile working apparatus 15f-2 comprising a rotatable drive shaft is inserted through the rearward end 28 of the sterility barrier, advanced through the sterility barrier, through the proximal connector 22 and through the sealed lumen 18f until its tapered distal end 92 becomes seated within and engaged with the concave idler member 75. A motor 94 is connected to the drive shaft and is used to rotatably drive the shaft causing concomitant rotation of the idler 75 and the gear 90 that is co-axially mounted on the drive shaft. The drive shaft gear 90 is enmeshed with the central gear 76 and causes concomitant rotation of the central gear 76. The central gear 76 is enmeshed with the other gear 84, thereby causing concomitant rotation of the other gear 84, and its axle 86 and the attached atherectomy cutter 71. The operator then advances, retracts and/or rotates the catheter body 12f within the blood vessel, as necessary, to effect severance of the occlusive matter. In the particular embodiment shown, the atherectomy cutter 71 reduces the severed matter to particles that are small enough to be released into the bloodstream without deleterious consequence. Alternatively, however, the atherectomy catheter device 10f may additionally incorporate an aspiration lumen through which severed particles of atherosclerotic plaque or other matter may be aspirated in the proximal direction through the catheter body 12f. Or, the atherectomy catheter device 10f may incorporate or be used in conjunction with a distal protection apparatus such as those described in U.S. Pat. No. 4,794,928 (Kletschka) or U.S. Pat. No. 4,873,978 (Ginsburg) to catch and contain any severed particles that are released into the patient's bloodstream. Although the device 10f described above utilizes two (2) working apparatus, namely a first working apparatus comprising 15f-1 comprising an IVUS and a second working apparatus 15f-2 comprising a drive shaft, it may be desirable for the drive shaft to be permanently disposed within the device such that the IVUS may remain disposed within the sealed lumen 18f during the operation of the atherectomy cutter 71 such that the IVUS may be used to visualize and guide the movement of the atherectomy cutter 71 and to guard against erroneous perforation of the blood vessel wall or other undesirable consequences during the actual severing of the occlusive matter by the atherectomy cutter. Also, although this embodiment of the device 10f incorporates an atherectomy cutter 71 of the side-cutting type, it will be appreciated that an end-cutting atherectomy cutter located at the distal end of the catheter body 12f may alternatively be used. One such end-cutting atherectomy cutter is described in U.S. Pat. No. 5,432,799 (Shiu), the entire disclosure of which is expressly incorporated herein by reference.

G. Guide Catheter Device with Vessel Occluder or Other Catheter-Deployable Intraluminal Implant FIGS. 9–9b show a guide catheter device 10g (FIG. 9) of the present invention along with a vessel occluder 110 (FIG. 9b) and a pusher 112 (FIG. 9a) that are usable in conjunction with the guide catheter device 10g.

This guide catheter device 10g incorporates all of the elements of the basic catheter device 10 shown in FIG. 1 and described above, including an elongate catheter body 12g, a hand piece 14g, a through-lumen 16g that extends longitudinally from the proximal end of the hand piece 14g to the distal end DE of the catheter body 12g and a sealed lumen 18g that extends from a connector 22 mounted on the hand piece 14g, through the hand piece 14g and longitudinally through the catheter body 12g to a closed distal end 20g. Also, as in each of the above-described embodiments, the forward end 26 of the tubular sterility barrier 24 is attached to the proximal connector 22 such that the sealed lumen 18 leads into the interior of the tubular sterility barrier 24.

In routine operation, a distal portion DP of the catheter body 12g is inserted into the patient's body while a proximal portion PP of the device 10g remains exteriorized. A sterile field SF is maintained around the proximal portion PP of the catheter device 10g, as denoted by dotted lines on FIG. 9. The sterility barrier 24 extends through the sterile field SF such that the rearward end 28 of the sterility barrier 24 is located outside of the sterile field SF. As described in detail elsewhere in this patent application, the attachment between the forward end 26 of the sterility barrier 24 and proximal connector 22 is sufficiently sealed to prevent any microbes introduced within the interior of the sterility barrier 24 and/or within the interior of the sealed lumen 18 from escaping into the sterile field SF. Also, no openings are formed between the sealed lumen 18g and the outer surface of the distal portion DP of the catheter body 12g such that, when the distal portion DP is inserted into a patients body, any microbes that the become introduced into the sealed lumen 18g will be contained within the catheter body 12g and will not escape into the patient's body.

The preferred construction of this guide catheter 10g has been described on pages 33–34 and in FIGS. 4–6 of PCT International Publication No. WO99/49793, the entirety of which is expressly incorporated herein by reference. In particular, this guide catheter 10g incorporates a braid 114 disposed within the wall of a braided portion BP of the catheter body 12g. This braid 114 enhances the column strength and torquability of the catheter body 12g. The sealed lumen 16g extends distally beyond the distal end 118 of the braid 114 such that a distal segment 116 of the sealed lumen is not surrounded by the braid 114 and is permeable by ultrasound of the type emitted from and received by an intravascular ultrasound imaging (IVUS) device. Alternatively, a non-metallic braiding material such as a polymer material may be used to allow the braid 114 to extend all the way to the distal end of the catheter body 12g without blocking or interfering with the desired passage of ultrasound through the distal portion of the catheter body 12g. In this regard, a working apparatus 15g that comprises an intravascular ultrasound imaging (IVUS) catheter may be inserted into the rearward end 28 of the sterility barrier 24, then through the connector 22 and advanced through the sealed lumen 18g until the transducer of the IVUS device is located within the ultrasound-permeable distal segment 116 of sealed lumen 18g. When so positioned, the IVUS device may be used to the image the surrounding walls of the vessel or anatomical structure in which the catheter body 12g is positioned and/or other anatomical structure's surrounding that vessel or anatomical structure. As will be appreciated by those of skill in the art, the ability to introduce an imaging device into the interior of a guide catheter may prove useful in numerous medical procedures were it is desirable to image the vessel within which the guide catheter is positioned and/or nearby anatomical structures.

One example of such a procedure is the delivery of an intraluminal or blocker into a blood vessel, such as a coronary vein, to fully or partially block the flow of blood through the vein, as described in PCT International Publication WO97/27893, the entire disclosure of which is expressly incorporated herein by reference. In this regard, FIG. 9b shows an example of a radially expandable intraluminal blocker apparatus 110 and FIG. 9a shows an example of a pusher 112 that is usable to the deliver the blocker apparatus 110 out of the distal end of the through lumen 16g of the guide catheter device 10g. The blocker 110 generally comprises a resilient wire frame 128 having a cover of elastomeric material, polytetrafluoroethylene (PTFE) film or other suitable material disposed thereon. The blocker 110 is compressable to a radially compact configuration, but when uncompressed will self-expand to its radially expanded configuration as shown in FIG. 9b.

In typical operation, the guide catheter device 10g is inserted into the patient's vasculature using sterile technique, as described here above in relation to the basic catheter device 10 of FIG. 1. In applications where the guide catheter 10g is to be advanced into a coronary vein, a larger coronary sinus guide catheter such as that described in, and shown in FIGS. 11–11a of, PCT International Publication No. WO99/49793 may be initially positioned in the coronary venous sinus, and this guide catheter 10g will then be advanced over a guidewire and through the lumen of the coronary sinus guide catheter, into the desired coronary vein. Thereafter, the guidewire over which this guide catheter 10g was advanced into the coronary vein may be retracted and removed and a working apparatus 15g that comprises an IVUS imaging device will be advanced through the sterility barrier 24 and into the sealed lumen 16g to a position where the transducer of the IVUS device is located within the ultrasound permeable distal portion 116 of the sealed lumen 16g. Thereafter, the IVUS may be used to visualize the wall of the coronary vein that surrounds the distal portion of the catheter body 12g and such image may be used to obtain a precise determination of the luminal diameter of that region of the coronary vein. Based on the diameter measurement obtained through use of the IVUS imaging device, a blocker 110 will be selected that has a diameter slightly larger than the luminal diameter of the coronary vein when in its fully radially expanded configuration. Because a precise measurement of the vein's luminal diameter has been obtained by the IVUS imaging device, the operator need not guess or speculate as to the correct size of blocker 110 to be used. This enables precise size-matching of the blocker 110 to the luminal diameter of the blood vessel, thereby minimizing the potential for slippage, movement or dislodgement of the blocker 110 due to undersizing of the blocker relative to the luminal diameter of the vessel or for over-dilation, perforation or erosion of the vessel wall due to over-sizing of the blocker 110 relative to the luminal diameter of the vessel. After a blocker 110 of the correct size has been selected, it will be compressed into its radially compact configuration and inserted into the through lumen 16g of the guide catheter device 10g. Thereafter, the distal end 124 of the pusher 112 will be advanced into the proximal end of the through lumen 16g. The operator will then grasp the handle 126 of the pusher 112 and will advance the pusher through the lumen 16g to push or expel the blocker 110 out of the distal end of the through lumen 16g. As it emerges from the distal end of the catheter device 10g, the blocker 110 will self-expand into frictional engagement with the surrounding wall of the coronary vein such that the cover 130 of the blocker 110 will fully or partially block the flow of blood in at least one direction through the coronary vein. After the blocker 110 has been implanted in the vein lumen, the IVUS imaging device may once again be used to verify the proper placement and function of the blocker. 110.

Although described above and shown in FIGS. 9–9b with reference to placement of vascular blockers or occluders, it is to be appreciated that the guide catheter device 10g may be useable to deliver may other types of radially expandable apparatus at specific sites within the body. Examples of other types of radially expandable, implantable apparatus that may be delivered by the guide catheter 10g include but are not limited to self expanding stents, stent-grafts, clips, connectors, anastomotic clips, occlusion coils, endovascular grafts, etc.

H. Construction and Modification of the Sterility Barrier

As described hereabove, the tubular sterility barrier 28 that is included in all embodiments of the invention preferably comprises a tube formed of pliable or flexible plastic film or plastic sheet, such as polyethylene of 1 to 5 mils thickness. In many applications, it will be desirable for the material of which the sterility barrier 24 is formed to be clear or transparent so that the operator may see the non-sterile working apparatus 15 within the interior of the tubular sterility barrier 24.

Figure 8:
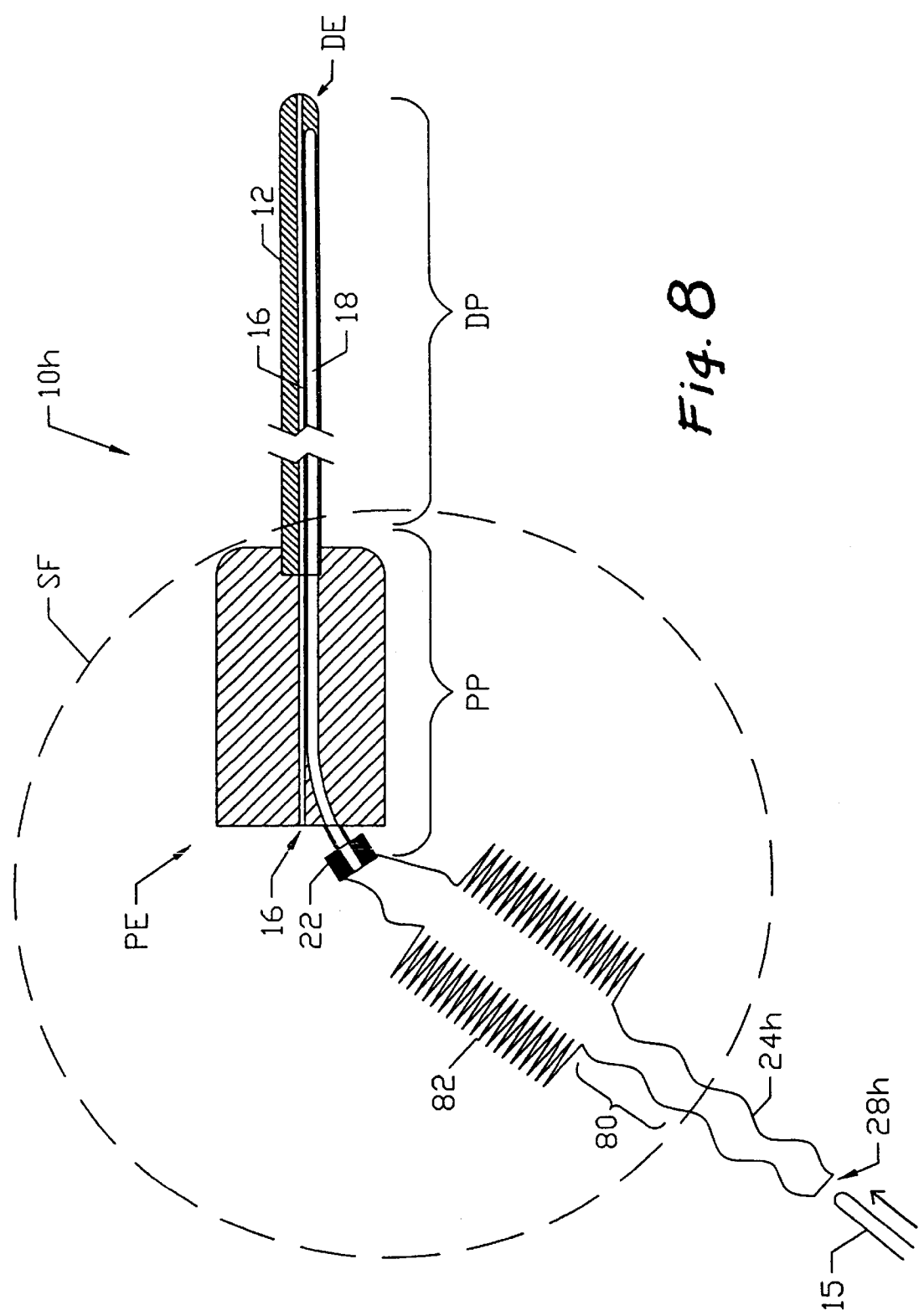
FIG. 8 is a longitudinal sectional view of a basic catheter device of the present invention that incorporates a sterility barrier having an accordion section to facilitate longitudinal advancement and/or retraction of a second catheter or other elongated apparatus within the seal lumen of the catheter device.

Additionally, in many applications it will be desirable for the sterility barrier 24 to be sufficiently light and flexible to allow the operator to place his/her gloved hand on the sterile outer surface of the sterility barrier 24, to grasp the non-sterile working apparatus 15 of through the sterility barrier 24, and to thereby advance or retract the non-sterile working apparatus 15 within the sealed lumen 18. In this regard, a multiplicity of bumps, ribs, projections or other grasp-enhancing surface disruptions may be formed on the outer surface of the sterility barrier 24 to aid the operator in grasping, advancing and/or retracting the working apparatus 15 through the easterly the barrier 24. Also, as the operator grasps and advances the working apparatus 15 through the tubular barrier 24 it will typically be necessary for the sterility barrier to become slackened, compressed, convoluted or "bunched up" in the area ahead of the operator's hand. Provided that the sterility barrier 24 is formed of material that is sufficiently thin and flexible such slackening, compression, convolution or bunching up of the sterility barrier ahead of the operator's hand should not present a problem. Optionally, as shown in FIG. 8, a modified catheter device 10h may incorporate a tubular sterility barrier 24h that is formed of the above-described material but which is specifically constructed to facilitate such slackening, compression, convolution or bunching up of the sterility barrier 24h ahead of the location 80 at operator's hand. This modified sterility barrier 24a incorporates a longitudinally shortenable region 82 that is constructed to easily collapse or shorten, such as a series of living hinges and/or one or more zig-zag sections in the nature of an accordion configuration formed in the barrier 24h at location(s) distal to the operator's hand placement location 80. In this manner, as the operator grasps the non-sterile working apparatus 15 through the hand placement region of the sterility barrier 24h and advances the working apparatus 15 in the distal direction through the sealed lumen 18 thereby causing the longitudinally shortenable region 82 to collapse and shorten as shown in FIG. 8. Subsequently, when it is desired to retract or withdraw the working apparatus 15, the operator may again grasp the working apparatus through the hand placement region 80 of the sterility barrier 24h and pull working apparatus 15 in the proximal direction, thereby causing the longitudinally shortenable region 82 to become extended and to return to its non-collapsed configuration. In this embodiment, the tubular sterility barrier 24h will be of sufficient length to allow its rearward end 28h to remain outside of the sterile field SF even when the longitudinally shortenable region 82 is fully collapsed, as shown in FIG. 8.

I. Sealing or Connection of the Tubular Sterility Barrier to the Catheter

In order to perform its intended function of containing microbial contamination and preventing microbes or other contaminants from entering the sterile field SF, it is important that the forward end 26 of the sterility barrier 24 be sealed to the connector to 22, the hand piece 14 or elsewhere on the catheter device 10 in such a manner as to prevent microbial contamination from escaping through such seal. Accordingly, the forward end 26 of the sterility barrier 24 may be sealed to the connector to 22, the hand piece 14 or elsewhere on the catheter device 10 by heat sealing, solvent welding, ultrasonic welding, adhesive or other appropriate, microbially non-traverseable means.

In some embodiments, it may be desirable for the sterility barrier 24 to be detachable from the remainder of the catheter device 10 such that clinicians selectively attach and detach the sterility barrier at will. An example of the catheter device 10i having a detachable sterility barrier 24i is shown in FIGS. 10 and 10a. With reference to FIGS. 10 and 10a, this catheter device 10i incorporates a number of the elements of the basic catheter device 10 of FIG. 1, including an elongate catheter body 12i, a hand piece 14i, a through-lumen 16i that extends longitudinally from the proximal end of the hand piece 14i to the distal end DE of the catheter body 12i and a sealed lumen 18i that extends from a connector 22i mounted on the hand piece 14i, through the hand piece 14i and longitudinally through the catheter body 12i to a closed distal end 20i. The connector 22i of this embodiment has threads 140 formed about its outer surface. A detachable tubular sterility barrier 24i has an internally threaded connector 142 formed un its forward end 26i. A cylindrical projection 146 is formed within connector 142 and the forward end 26i of the sterility barrier 24i is continuous with cylindrical projection 146 such that the interior canal of the tubular sterility barrier 24i leads directly into the interior of the cylindrical projection 146. A compressible elastomeric washer 150 is disposed transversely within the proximal connector 22i. The threads 144 formed about the inner surface of the sterility barrier's connector 142 are engageable with the threads 140 formed on the outer surface of the catheter's proximal connector 22i. In this manner, the connector 142 on the forward end 26i of the sterility barrier 24i may be screwed on to the proximal connector 22i formed on the hand piece 14i of the catheter device 10i causing the distal face 148 of the cylindrical member 146 to compress against the elastomeric washer 150 and form a seal between the two connectors 142, 22i that will prevent any bacteria, viruses, parasites or other microbes that may be into the interior of the sterility barrier 24i or sealed lumen 16i from escaping into the sterile field SF.

It is to be understood and appreciated that the invention has been described herein with reference to certain presently preferred embodiments and examples only, and no effort has been made to exhaustively describe all possible embodiments and examples of the invention. Indeed, as those killed in the art will appreciate, various additions, deletions, modifications and variations may be made to the particular embodiments and examples described hereabove without departing from the intended spirit and scope of the invention. Accordingly, it is intended that all such additions, deletions, modifications and variations be included within the scope of the following claims.

What is claimed is:

1. A tissue penetrating catheter device useable, in conjunction with a separate imaging apparatus, to penetrate from the lumen of a patient's blood vessel, outwardly through the wall of that blood vessel, and to a target location within the patient's body, said tissue penetrating catheter device comprising:
    a) a flexible catheter body having i) a proximal end, ii) a distal portion that is insertable into the blood vessel, iii) a penetrator outlet formed in the distal portion, iv) an imaging apparatus inlet located proximal to the distal portion and v) an imaging lumen that extends from the imaging apparatus inlet into the distal portion of the catheter body, at least the portion of the imaging lumen located within the distal portion of the catheter body being sealed such that any microbial contamination introduced thereinto will not escape into the patients body when the distal portion of the catheter body is positioned within a blood vessel, vi) a penetrator passable out of the penetrator outlet, and vii) trajectory determining apparatus useable in conjunction with a separate imaging apparatus to determine the trajectory along which the penetrator will advance from the catheter body; and
    b) a generally tubular sterility barrier, one end of said sterility barrier being secured about the imaging apparatus inlet such that an elongate imaging apparatus may be passed through the tubular sterility barrier, through the imaging apparatus inlet and to an operative position within the imaging lumen to permit the imaging apparatus to be used to obtain an image of the penetrator and the target location.

2. A system comprising a catheter device according to claim 1 in combination with an elongate imaging apparatus that is sized for insertion into the imaging lumen of the catheter device.

3. A system according to claim 2 wherein the imaging apparatus comprises an ultrasonic imaging catheter.

4. A system according to claim 2 wherein the imaging apparatus comprises an ultrasonic imaging wire.

5. A system according to claim 2 wherein the catheter device is sterile and the imaging apparatus is non-sterile.

6. A catheter device according to claim 1 wherein the trajectory determining apparatus includes at least one marker formed on the catheter to indicate the direction in which the penetrator will pass from the catheter body.

7. A catheter device according to claim 6 wherein:
    the marker comprises an imageable member located at a radial position that is in known alignment with the direction in which the penetrator will extend when deployed from the catheter.

8. A catheter device according to claim 6 wherein:
    the marker comprises a plurality of elongate members that extend longitudinally, at circumferentially spaced-apart locations about the catheter;
    the imaging lumen extends into a location amidst said elongate members;
    a first one of the elongate members is located at a radial position that is in known alignment with the direction in which the penetrator will extend when deployed from the catheter; and,
    the imaging apparatus, when in its operative position, is capable of providing an image of the marker, the image of the marker thereby enabling the operator to ratationally orient the catheter body in the blood vessel such that when the penetrator is subsequently deployed it will pass to the target location.

9. A catheter device according to claim 1 wherein the penetrator comprises a flow of energy.

10. A catheter device according to claim 9 wherein the penetrator is a laser beam.

11. A catheter device according to claim 1 wherein the penetrator comprises an elongate penetrating member.

12. A catheter device according to claim 11 wherein a guidewire lumen extends longitudinally through the tissue penetrating member.

13. A catheter device according to claim 1 wherein the sterility barrier is permanently sealed to the remainder of the catheter device by a microbe-tight seal.

14. A catheter device according to claim 1 wherein the sterility barrier is attachable to and detachable from the remainder of the catheter device by a microbe-tight seal.

15. A catheter device according to claim 1 wherein the penetrator is resilient and has a distal portion, the distal portion of the penetrator being preformed to a curved configuration, said penetrator being longitudinally retractable into the catheter body and longitudinally advanceable out of the catheter body.

16. A catheter device according to claim 1 wherein the sterility barrier is permanently attached to the catheter device.

17. A catheter device according to claim 1 wherein the sterility barrier is detachable from the catheter device.

18. A catheter device according to claim 1 further comprising a hand piece on the proximal end of the catheter body, said imaging apparatus inlet being formed on the hand piece.

19. A catheter device according to claim 1 wherein the sterility barrier is formed of flexible polymer material having a thickness of approximately 1–5 mils.

20. A catheter device according to claim 1 wherein the sterility barrier is substantially transparent.

21. A catheter device according to claim 1 wherein the sterility barrier is sufficiently flexible to allow the operator to grasp the working apparatus through the sterility barrier and to thereby advance the working apparatus into the lumen.

* * * * *